United States Patent
Roller et al.

(10) Patent No.: US 7,192,782 B2
(45) Date of Patent: Mar. 20, 2007

(54) METHOD AND APPARATUS FOR DETERMINING MARKER GAS CONCENTRATION IN EXHALED BREATH USING AN INTERNAL CALIBRATING GAS

(75) Inventors: Chad Roller, Houston, TX (US); Khosrow Namjou, Norman, OK (US); James Jeffers, Norman, OK (US)

(73) Assignee: Ekips Technologies, Inc., Norman, OK (US)

( * ) Notice: Subject to any disclaimer, the term of this patent is extended or adjusted under 35 U.S.C. 154(b) by 620 days.

(21) Appl. No.: 10/338,353

(22) Filed: Jan. 8, 2003

(65) Prior Publication Data

US 2003/0134427 A1    Jul. 17, 2003

Related U.S. Application Data

(60) Provisional application No. 60/347,513, filed on Jan. 11, 2002.

(51) Int. Cl.
*G01N 33/00* (2006.01)
*G01N 21/00* (2006.01)

(52) U.S. Cl. ............. 436/116; 436/133; 436/164; 436/171; 422/84; 422/55

(58) Field of Classification Search ............ None
See application file for complete search history.

(56) References Cited

U.S. PATENT DOCUMENTS

| | | | |
|---|---|---|---|
| 5,447,165 A | 9/1995 | Gustafsson | |
| 5,464,983 A | 11/1995 | Wang | |
| 5,640,014 A | 6/1997 | Sauke et al. | |
| 5,922,610 A | 7/1999 | Alving et al. | |
| 6,010,459 A | 1/2000 | Silkoff et al. | |
| 6,038,913 A | 3/2000 | Gustafsson et al. | |
| 6,099,480 A | 8/2000 | Gustafsson | |
| 6,363,772 B1 * | 4/2002 | Berry | 73/24.02 |
| 6,412,333 B2 | 7/2002 | Inoue et al. | |
| 6,419,634 B1 | 7/2002 | Gaston, IV et al. | |

OTHER PUBLICATIONS

Roller et al. "Simulatneous NO and CO2 measurement in human breath with a single IV-VI mid-infrared laser", Optics Letters, 2002, v. 27, No. 2, pp. 107-109.*
Menzel et al. "Spectroscopic detection of biological NO with a quantum cascade laser", Appl. Phys. B, 2001, v. 72, pp. 859-863.*

* cited by examiner

*Primary Examiner*—Yelena G. Gakh
(74) *Attorney, Agent, or Firm*—Tomlinson & O'Connell, PC

(57) ABSTRACT

A method and an apparatus for measuring the concentration of a specific gas component of a gas mixture including another gas whose concentration is independently known using light absorption spectroscopy are provided. A method and an apparatus for assessing human airway inflammation by measuring the concentration of exhaled NO and $CO_2$ present in orally exhaled breath using light absorption spectroscopy are also provided. NO concentration is determined at the time during breath sampling corresponding to a known exhaled $CO_2$ concentration. Methods and apparatus are further provided for measuring NO concentration in orally exhaled human breath that analyze breath emanating from the lower airways and lungs, while excluding breath from the nasal cavity. They include steps and apparatus for discarding initially exhaled breath, flowing breath through an analysis chamber using a vacuum pump and flowing breath through an analysis chamber using a vacuum pump at an initial flow rate and later at a flow rate higher than the initial flow rate.

25 Claims, 19 Drawing Sheets

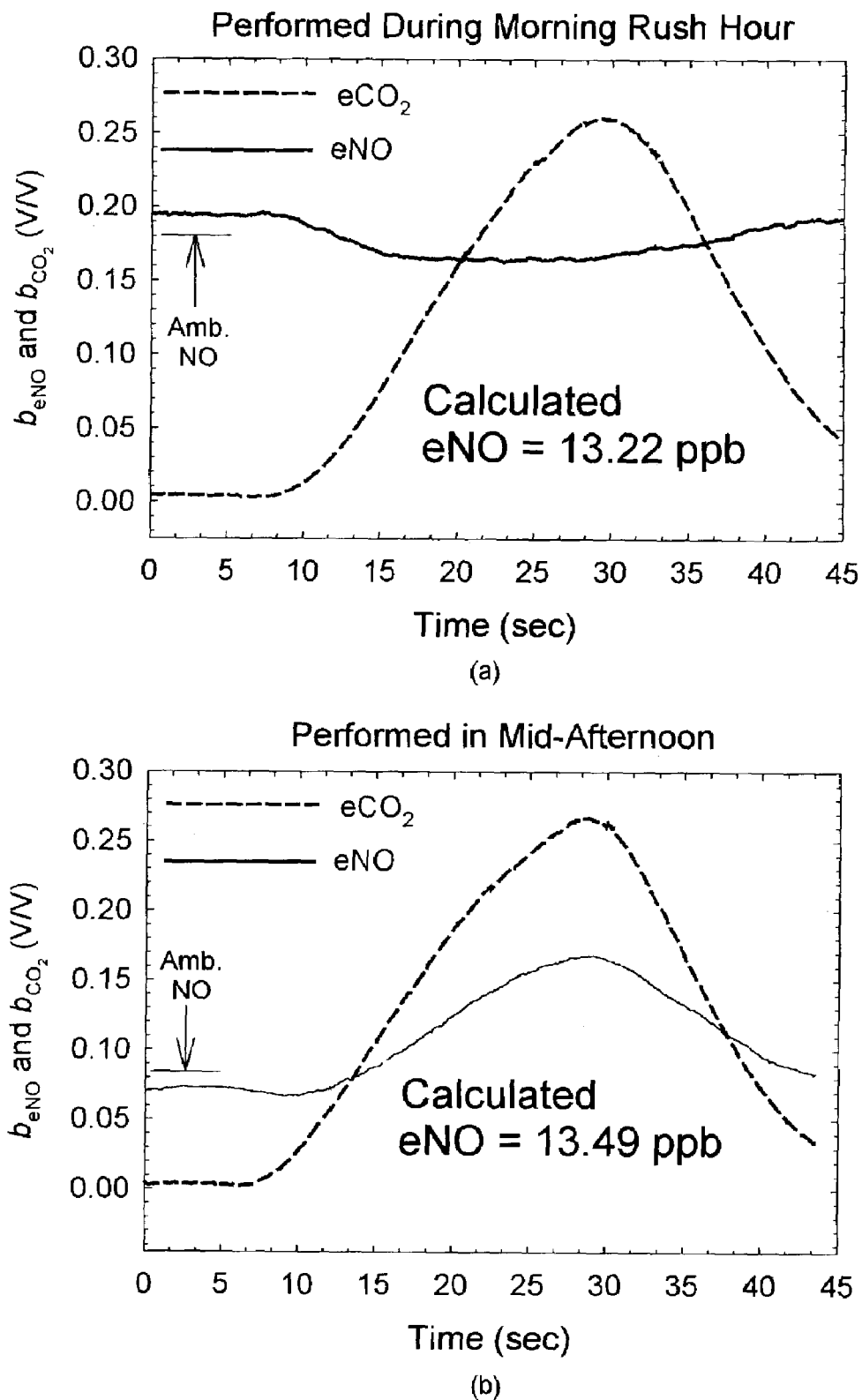
Figure 18 (a) and 18(b)

METHOD AND APPARATUS FOR DETERMINING MARKER GAS CONCENTRATION IN EXHALED BREATH USING AN INTERNAL CALIBRATING GAS

This application claims the benefit of U.S. Patent Application No. 60/347,513 filed Jan. 11, 2002.

BACKGROUND OF THE INVENTION

1. Field of the Invention

The invention relates to methods and apparatus for determining the concentration of a gas in a mixture.

2. Description of the Prior Art

Gas mixtures are routinely analyzed in fields ranging from medical diagnostics to automobile design. Techniques used vary widely and include mass spectroscopy, infrared spectroscopy, chemiluminescence and flame ionization. Regardless of the application, accuracy, reliability, convenient operation, low cost and preferably real-time analysis results are desirable. In the field of medical diagnostics, convenient, patient-friendly operation and real-time delivery of results are crucial for successful clinical implementation.

Currently available methods for determining the concentration of a gas in a mixture typically require use of a reference as in U.S. Pat. No. 5,640,014 to Sauke et al. wherein a reference signal or reference gas is used in a diode laser spectroscopy method to determine the isotopic ratio of a gas in a sample. Other methods involve deliberate introduction of a trace gas to the gas mixture to be analyzed as in U.S. Pat. No. 6,412,333 to Inoue et al. U.S. Pat. No. 6,412,333 describes an auto exhaust analyzer system and method wherein a trace gas is introduced into the exhaust gas stream, the mass of the trace gas is calculated using the analyzer and the calculated mass then compared with the known mass of trace gas to verify the accuracy of the analysis. Still other techniques compensate for inaccuracy in non-dispersive infrared analysis using signal processing techniques such as U.S. Pat. No. 5,464,983 to Wang which describes measurement of change of signal (CS) and change of change of signal (CCS) and comparison of CCS data obtained to CCS data for known gases at known concentrations and temperatures.

In the field of medical diagnostics, nitrogen monoxide (NO) is a well-established indicator of pulmonary function. Analysis of exhaled nitric oxide provides a health care provider with a non-invasive test for inflammatory diseases of the lower airways such as asthma. Widely used diagnostic tests for asthma such as spirometry give only limited and indirect information about lower airway inflammation. Current methods measuring exhaled NO for assessing lung function, such as U.S. Pat. No. 5,447,165 to Gustafsson, use mass spectroscopy and chemiluminescence to measure the time distribution of NO formed during exhalation and require that results be compared with unimpaired lung function of a living subject reference. U.S. Pat. No. 6,099,480 to Gustafsson describes collection of human breath and analysis for NO content using chemiluminescence or reagent-based chemical analysis techniques. U.S. Pat. No. 6,419,634 to Gaston et al. uses reagent-based calorimetric NO assay analysis of exhaled human breath condensate to evaluate airway inflammation.

Endogenous nitric oxide emanating from the airways and lungs is the preferred indicator of airway inflammation. Hence, breath collection techniques to collect this endogenous nitric oxide while excluding exhaled nasal NO from study have been developed. U.S. Pat. No. 6,010,459 to Silkoff et al. requires a patient to exhale at a constant rate and increases pressure in the mouth to close off the nasopharynx during exhalation thereby excluding nasal NO. U.S. Pat. No. 6,038,913 to Gustafsson et al. requires that a patient exhale against a back pressure during the later phase of an exhalation. U.S. Pat. No. 5,922,610 to Alving et al. describes a face mask that tightly covers the nose and/or mouth of the subject. Such techniques that require controlled exhalation by a patient can be difficult for those patients with impaired respiratory function and especially for pediatric patients. All of these methods require frequent calibration of the NO sensor using a calibration gas with a known NO concentration. This requirement complicates use of such sensing technology in a clinical setting.

Thus, there exists a need for accurately determining the concentration of a specific gas of interest in an as-obtained gas mixture sample without introduction of any additional reference gas. There exists further need for accurately assessing airway inflammation, using a single exhaled breath from a single patient without any healthy lung function reference. Preferably, such airway inflammation assessment is conveniently conducted in a clinical setting, maximizes patient comfort and provides real-time results that can enable a health care provider to diagnose and treat a patient in a single clinic visit

SUMMARY OF THE INVENTION

The present method is directed to a method for comparing a level of a marker gas to a level of a calibration gas. The marker gas and the calibration gas are present in an exhaled breath sample. The method comprises obtaining the exhaled breath sample over an exhaled breath sampling interval. The exhaled breath sample includes the marker gas and the calibration gas. The calibration gas is intrinsic to the exhaled breath sample and has an independently known concentration that is variable within an acceptable range. The method further includes providing a spectrometer including a spectrometer light source, a spectrometer gas sample cell, a spectrometer detector and a spectrometer computer. The exhaled breath sample is placed in the spectrometer gas sample cell and illuminated with the spectrometer light beam. The light beam from the spectrometer light source is passed through the exhaled breath sample and detected with the spectrometer detector to produce a signal sampling characteristic of the exhaled breath sample. A breath sample spectrum is generated from the signal sampling and stored in the spectrometer computer. The breath sample spectrum is analyzed using said spectrometer computer. The analysis includes identifying an absorption characteristic of the marker gas and an absorption characteristic of the calibration gas. Marker gas absorption intensity and a calibration gas absorption intensity are determined and stored as a function of time over said exhaled breath sampling interval. The generating and analyzing steps are repeated to produce a series of breath sample spectra. Each spectrum has an absorption characteristic of the marker gas and the calibration gas. A single breath sample spectrum where a known concentration calibration gas absorption corresponds to an independently known calibration gas concentration and a simultaneous marker gas absorption is identified. A ratio of said simultaneous marker gas absorption intensity to said known concentration calibration gas absorption intensity is calculated and multiplied by a proportionality constant to determine the concentration of said marker gas.

The present invention is further directed to a method for assessing human airway inflammation. The method comprises collecting an exhaled human breath sample over an exhalation interval. The exhaled human breath sample comprises exhaled NO and exhaled $CO_2$. A spectrometer including a spectrometer light source, a spectrometer gas sample cell, a spectrometer detector and a spectrometer computer are provided. The exhaled human breath sample is placed in said spectrometer gas sample cell and illuminated with a spectrometer light beam. The light beam is passed through said exhaled human breath sample and detected with the spectrometer detector to produce a signal sampling and generating a human breath sample spectrum from the signal sampling. The human breath sample spectrum is analyzed using said spectrometer computer. The analysis includes identifying an absorption characteristic of exhaled NO and an absorption characteristic of exhaled $CO_2$ and determining an exhaled NO absorption intensity and an exhaled $CO_2$ absorption intensity. The exhaled NO absorption intensity and exhaled $CO_2$ absorption intensity are stored as a function of time over the exhalation interval. The steps of analyzing and generating are repeated to produce a series of breath sample spectra. Each spectrum has an absorption that is characteristic of the exhaled NO and the exhaled $CO_2$. A single signal sampling interval wherein a known concentration $CO_2$ gas absorption which corresponds to an independently known $CO_2$ gas concentration and a simultaneous NO absorption is identified. A ratio of said simultaneous NO absorption intensity to said known concentration $CO_2$ gas absorption intensity is calculated and multiplied by a proportionality constant to obtain the concentration of said exhaled NO thereby providing an assessment of human airway inflammation.

The present invention further includes an apparatus for calculating a ratio of a marker gas to a calibration gas. Both the marker gas and the calibration gas are intrinsically present in an exhaled breath sample. The calibration gas is present in the gas mixture sample with an independently known concentration variable within an acceptable range. The apparatus further includes a spectrometer light source for illuminating said exhaled breath sample, a spectrometer gas sample cell, and a spectrometer detector for detecting light transmitted through said gas mixture sample. The spectrometer detector detects the light to generate a signal sampling characteristic of the exhaled breath sample. The apparatus further comprises a spectrometer computer comprising an executable program for repeatedly generating and analyzing said signal sampling for multiple signal sampling intervals to obtain a breath sample spectra. The breath sample spectra are stored and analyzed. Analysis of the spectra includes identifying a marker gas absorption characteristic and a calibration gas absorption characteristic and determining a marker gas absorption intensity and a calibration gas intensity. Marker gas absorption intensity and calibration gas absorption intensity are calculated as a function of time to identify a single signal sampling interval where a known concentration calibration gas absorption corresponds to an independently known calibration gas concentration and a simultaneous marker gas absorption. The ratio of said simultaneous marker gas absorption intensity to said known concentration calibration gas absorption intensity is calculated by multiplying said ratio by a proportionality constant to determine the concentration of said marker gas.

The present invention also includes an apparatus for assessing human airway inflammation. The apparatus comprises a spectrometer gas sample cell, a spectrometer light source, a spectrometer detector, and a spectrometer computer. The spectrometer gas sample cell is adapted to receive an exhaled human breath sample containing exhaled NO and exhaled $CO_2$. The spectrometer light source is adapted to generate a light for illuminating the exhaled human breath sample. The spectrometer detector is adapted to detect the light transmitted through said exhaled human breath sample to generate a signal sampling characteristic of the orally exhaled human breath sample. The spectrometer computer comprises an executable program adapted to analyze a human breath sample spectrum generated from the signal sampling. The program identifies an exhaled NO absorption and an exhaled $CO_2$ absorption and determines an exhaled NO absorption intensity and an exhaled $CO_2$ absorption intensity. The exhaled NO absorption intensity and said exhaled $CO_2$ absorption intensity are stored as a function of time. The program generates a series of human breath sample spectra. Each spectrum has an absorption characteristic of the exhaled NO and the exhaled $CO_2$. A single signal sampling interval where a known concentration $CO_2$ gas absorption which corresponds to an independently known $CO_2$ gas concentration and a simultaneous NO absorption occur is identified. A ratio of said simultaneous NO absorption intensity to said known concentration $CO_2$ gas absorption intensity is calculated and multiplied by a proportionality constant to obtain the concentration of said exhaled NO thereby providing an assessment of human airway inflammation.

A method for measuring NO concentration in orally exhaled human breath includes steps of having a human subject normally exhale a single breath into a mouthpiece. The first part of the single breath, initially exhaled human breath, is collected in a discard container and is discarded. The remainder of the single breath, the remaining orally exhaled human breath, is flowed to an NO analysis system where NO concentration is obtained through a tube connected to a vacuum pump.

An apparatus for measuring NO concentration in orally exhaled human breath including a mouthpiece for accepting orally exhaled human breath made up of initially exhaled human breath and remaining exhaled human breath is provided. The mouthpiece is connected to a discard container and to a flow tube, which is further connected to a vacuum pump and to a light absorption spectrometer system so that initially orally exhaled human breath is collected in the discard container and the remaining orally exhaled human breath is delivered to an NO analysis system where NO concentration is measured.

According to another method for measuring NO concentration in orally exhaled human breath, a human subject normally exhales a single breath, including initial orally exhaled human breath and remaining orally exhaled human breath into a mouthpiece. The single human breath is flowed through a tube connected to a vacuum pump and to an NO analysis system where the single human breath is analyzed to obtain NO concentration.

Another apparatus for measuring NO concentration in orally exhaled human breath includes a mouthpiece for accepting orally exhaled human breath, having initially exhaled human breath and remaining orally exhaled human breath from a human subject. The mouthpiece is connected to a vacuum pump and to an NO analysis system for obtaining NO concentration.

According to yet another method for measuring NO concentration in orally exhaled human breath, a human subject normally exhales a single breath into mouthpiece. The single breath is flowed from the mouthpiece to an NO analysis system through a tube connected to a vacuum pump and to the NO analysis system first at a first flow rate and later at a second flow rate, less than the first flow rate. The single breath is analyzed with the NO analysis system to obtain NO concentration.

Yet another apparatus is provided for measuring NO concentration in orally exhaled human breath. A mouthpiece for accepting a single orally exhaled human breath is connected to a flow tube. The flow tube is further connected to a vacuum pump and to an NO analysis system for obtaining NO concentration. The flow tube includes a flow rate controller for sequentially generating a first flow rate and a second flow rate less than the first flow rate.

Objects of the invention are to provide a method and apparatus for measuring the concentration of a gas of interest, a marker gas, in a gas mixture that inherently includes the marker gas as well as another gas, a calibration gas having an independently known concentration by obtaining and comparing spectroscopic absorption intensities for the marker gas and calibration gas corresponding to when the concentration of the calibration gas is known independently.

Other objects of the invention are to provide a method and apparatus for assessing human airway inflammation by measuring NO concentration in orally exhaled human breath. The $CO_2$ inherently present with NO in human breath has an independently known concentration and by obtaining and comparing spectroscopic absorption intensities for NO and $CO_2$ when the concentration of the $CO_2$ is known, NO concentration can be obtained.

Yet other objects of the invention are to provide a method and apparatus to measure NO concentration in orally exhaled human breath wherein the initial portion of a single orally exhaled breath is discarded so that the patient need only provide a single breath exhaled normally through the mouth.

Additional objects of the invention are to provide a method and apparatus to measure NO concentration in orally exhaled human breath wherein a single breath is delivered to a light absorption spectrometer system through a tube at a reduced pressure provided by a vacuum pump so that the patient need only provide a single breath exhaled normally through the mouth.

Further objects of the invention are to provide a method and apparatus to measure NO concentration in orally exhaled human breath wherein a single breath is delivered to an NO analysis system through a tube at a reduced pressure provided by a vacuum pump at two different flow rates, a first flow rate and then at a second flow rate less than the first flow rate so that the patient need only provide a single breath exhaled normally through the mouth.

Other and further objects, features, and advantages of the present invention will be readily apparent to those skilled in the art upon reading the description of the preferred embodiments which follows.

BRIEF DESCRIPTION OF THE DRAWINGS

FIGS. 18(a) and 18(b) are plots showing breath eNO and $eCO_2$ exhalation trends measured from a nonasthmatic subject at different ambient NO levels.

DESCRIPTION OF PREFERRED EMBODIMENTS

The invention provides a method and apparatus for spectroscopically measuring the concentration of a particular marker gas in a gas mixture using another gas inherently present in the mixture and whose concentration is known independently as an internal calibration gas. Thus, the invention obviates the need for a separate reference or for deliberate introduction of any reference or trace gas to the gas mixture.

Figure 1:
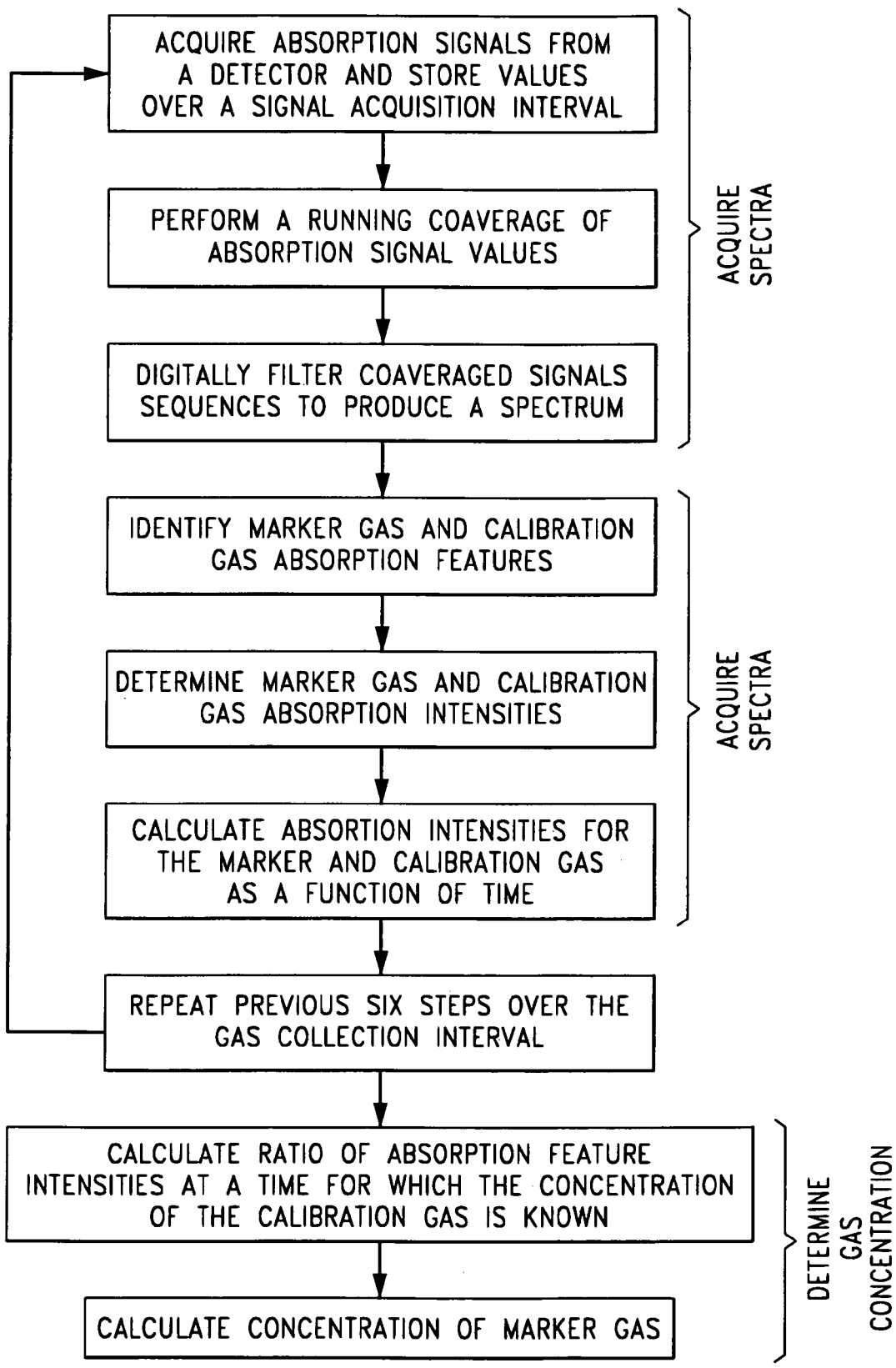
FIG. 1 is a block diagram summarizing steps of acquiring and analyzing gas mixture spectra to determine concentration of a gas mixture component.
Figure 2:
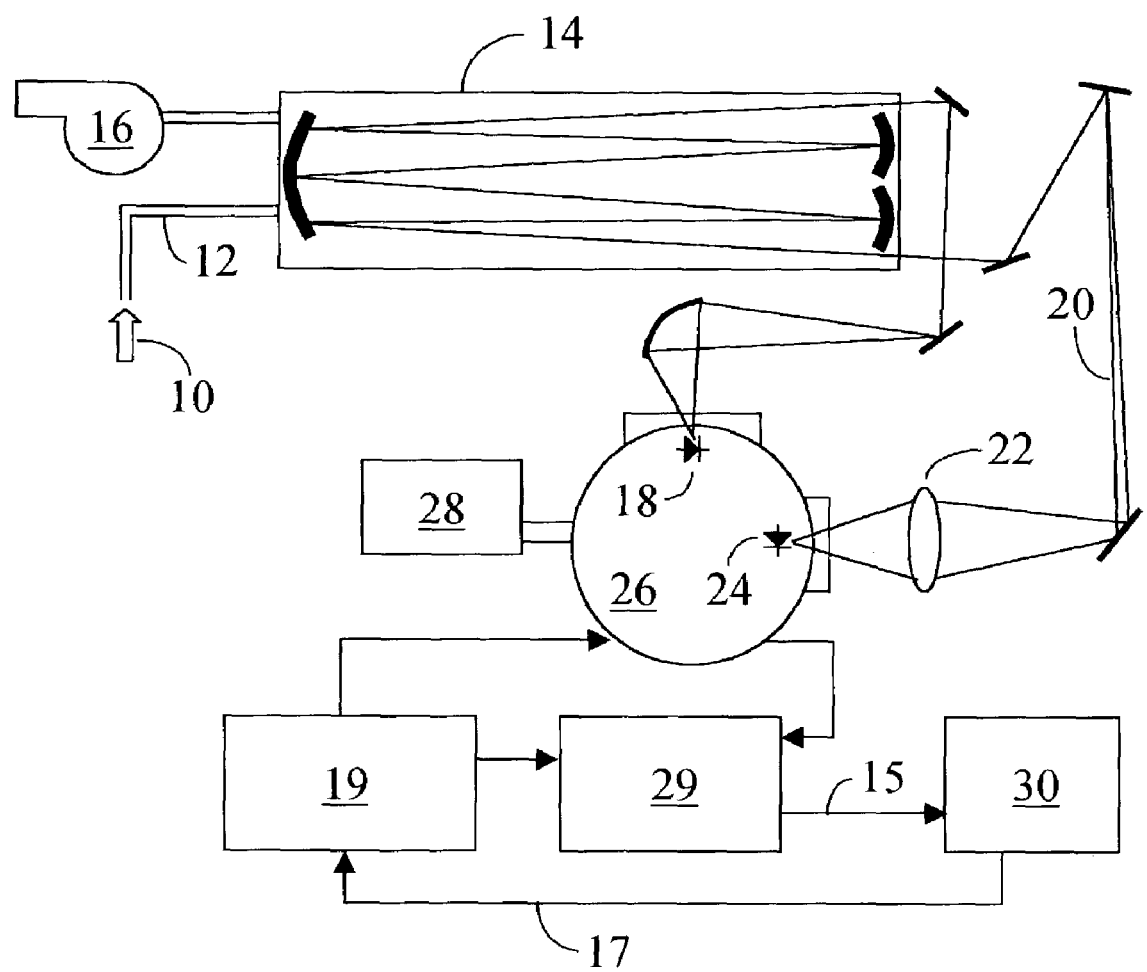
FIG. 2 is a schematic drawing of a gas mixture analysis system.

FIG. 2 shows a preferred embodiment of the invention. A gas mixture sample, represented by arrow 10 is introduced via tubing 12 into a spectrometer sample cell, specifically White cell 14. A Herriott cell can also be used as the spectrometer sample cell. Mechanical vacuum pump 16 evacuates White cell 14 to keep White cell 14 at a pressure selected to reduce line broadening and interference between the spectroscopic absorption associated respectively with the marker gas and calibration gas. Gas mixture sample 10 can be human breath having marker gases such as NO, $H_2O_2$, CO, $CO_2$, $CS_2$, $C_2H_6$, $CH_3O$, $NH_3$, $H_2S$, or OCS whose presence and concentration can be correlated with a disease. Calibration gases present in a human breath sample can be $CO_2$, $H_2O$, $N_2O$ or $CH_4$. The spectrometer can be a mid-infrared tunable laser absorption spectroscopy system where the spectrometer light source that illuminates the gas mixture sample is IV–VI diode laser 18 with an emission wavelength in the range of from about 3 µm to about 10 µm controlled by current driver/function generator assembly 19 and personal computer 30 as shown schematically by arrow 17.

Transmitted light beam 20 that has passed through gas mixture sample 10 in White cell 14 can be focused with lens 22 onto spectrometer detector 24 which is maintained with IV–VI diode laser 18 at reduced temperature in cryostat 26. Cryostat 26 is evacuated using ion pump 28. Spectrometer detector 24 generates a signal sequence which can be acquired by lock-in amplifier 29 after amplification by a preamp (not shown) and personal computer 30, equipped with an analog-to-digital (A/D) card to produce a gas mixture spectrum. The gas mixture spectrum can be a second harmonic absorption spectrum. Arrow 15 represents signals transmitted from lock-in amplifier 29 to personal computer 64. The gas mixture spectrum can be generated by digitally filtering a running co-average of at least two detector signal sequences which have been obtained and stored in personal computer 30 as stored detector electronic signal sequences.

The invention further provides a method and apparatus for assessing human airway inflammation by measuring the concentration of NO, a marker gas associated with human body tissue inflammation. The NO is present together with $CO_2$ in orally exhaled human breath. Since the concentration of $CO_2$ in orally exhaled human breath is known, it serves as an internal calibration gas. NO and $CO_2$ spectroscopic absorption intensities are identified, obtained and stored repeatedly to find a signal sampling interval wherein the $CO_2$ gas absorption intensity corresponds to a known $CO_2$ concentration. The $CO_2$ gas absorption intensity that corresponds to the independently known $CO_2$ concentration is the maximum $CO_2$ gas absorption intensity obtained over the entire time a human subject exhales, the exhalation interval. The NO gas absorption intensity obtained simultaneously with the $CO_2$ gas absorption intensity corresponding to an independently known $CO_2$ concentration in the range of from about 4% to about 5% is subsequently used in a ratio calculation to obtain the NO concentration which is an indicator for human airway inflammation. Exhaled NO concentration in the range of from about 5 parts per billion (ppb) to about 100 parts per billion (ppb) is indicative of airway inflammation.

Figure 4:
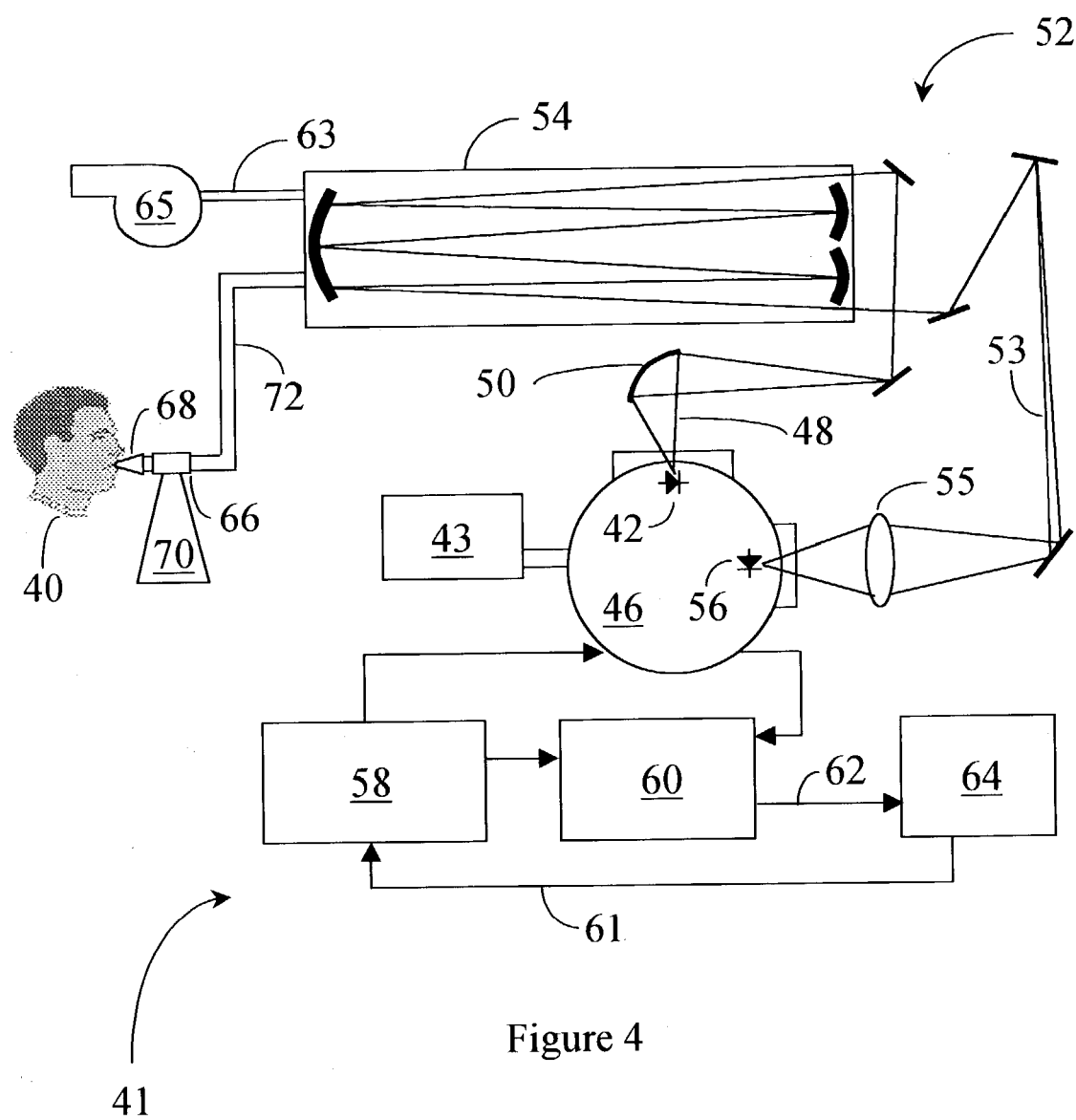
FIG. 4 is a schematic drawing of a breath collection and analysis apparatus and the TLAS system equipped with a IV–VI mid-infrared laser.

As shown in FIG. 4, human subject 40 orally exhales so that orally exhaled breath enters spectrometer system 41. Human subject 40 orally exhales into mouthpiece 68. Mouthpiece 68 is connected with T-piece 66, while T-piece 66 is further connected to discard container 70 and tubing 72. A one-way flutter valve, not shown, can be connected between T-piece 66 and discard container 70 to keep initially orally exhaled breath in discard container 70. All connections allow for passage of orally exhaled human breath. Tubing 72 carries orally exhaled breath to gas sample cell 54. Spectrometer gas sample cell 54, which can be a Herriott cell or multi-pass White cell, can be kept at a pressure chosen to reduce line broadening as well as interference between absorption characteristics associated, respectively, with the NO and $CO_2$ present in the orally exhaled breath sample. Human subject 40 can orally exhale a single breath as he or she would normally do while breathing not under test conditions so that breath provided at the beginning of the exhalation, initial exhaled breath, is collected in discard container 70 and is not analyzed by the spectrometer. After discard container 70 is filled, the rest of the breath from the single breath, remaining exhaled breath enters spectrometer gas sample cell 54 for spectroscopic analysis. Orally exhaled human breath can also be introduced into spectrometer gas sample cell 54 using mechanical vacuum pump 65 connected to spectrometer gas sample cell 54 by tubing 63 alone or together with the already described discard container 70 to induce flow of the orally exhaled human breath through spectrometer gas sample cell 54. The flow rate of orally exhaled human breath through spectrometer gas sample cell 54 can be varied using flow rate controllers not shown so that the breath first flows through spectrometer gas sample cell 54 at a first flow rate greater than a later, second flow rate.

Spectrometer system 41 can be a mid-infrared tunable laser absorption spectroscopy system and can have a IV–VI diode laser 42 with an emission wavelength in the range of from about 3 µm to about 10 µm as the light source to illuminate the orally exhaled human breath sample contained in gas sample cell 54. Spectrometer detector 56 generates detector electronic signal sequences in response to detection of light beam 53 that has been transmitted through the orally exhaled human breath sample contained in gas sample cell 54. Detector electronic signal sequences are acquired by lock-in amplifier 60 after amplification by a preamp (not shown) spectrometer computer 64 to generate a human breath sample spectrum which can be a second harmonic absorption spectrum. Arrow 62 represents signals transmitted from lock-in amplifier 60 to personal computer 64. A running co-average of at least two previously obtained and stored detector electronic signal sequences can be performed and the result digitally filtered to generate the human breath sample spectrum.

Figure 5:
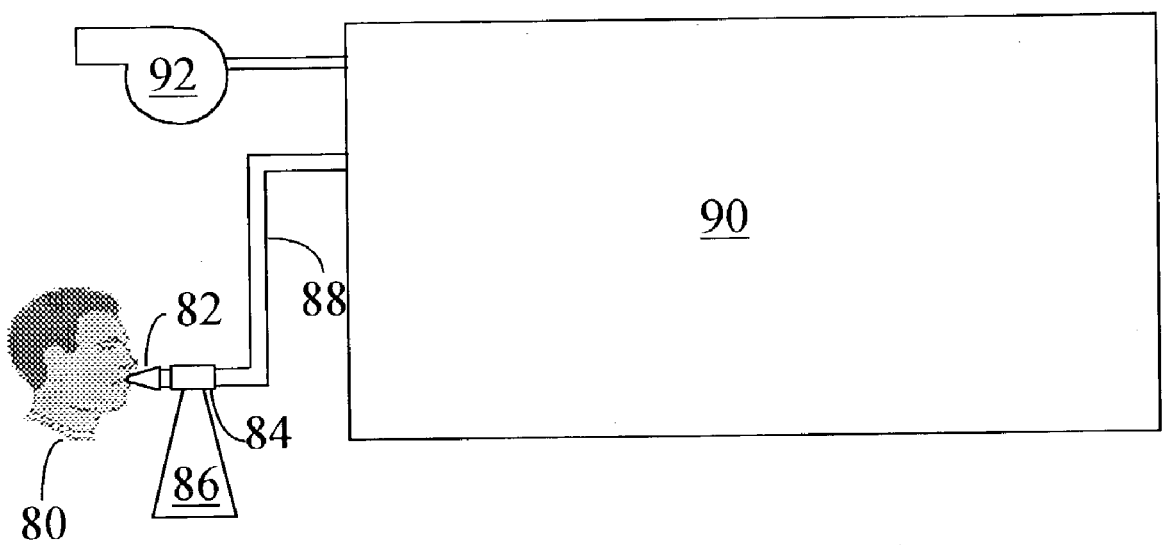
FIG. 5 is a schematic drawing of a breath collection and analysis apparatus including a container for collecting initially exhaled breath.

The invention also provides a method and apparatus for measuring NO concentration in orally exhaled human breath generally applicable for use with a wide variety of analysis systems capable of measuring NO concentration utilizing a discard container to eliminate initial exhaled breath from analysis. FIG. 5 shows human subject 80 orally exhaling a single breath as he or she would do when breathing normally, into mouthpiece 82 connected via T-piece 84 to discard container 86 and flow tube 88. Breath provided at the beginning of the exhalation, initial exhaled breath, is collected in discard container 86 and is discarded, i.e., not analyzed. After discard container 86 is filled, the rest of the breath from the single breath, remaining exhaled breath, enters NO analysis system 90 through flow tube 88. Mechanical vacuum pump 92 is connected to NO analysis system 90 and flow tube 88 so that orally exhaled human breath flows through the NO analysis system. Mechanical vacuum pump 92 can be operated to produce a vacuum in the range of from about 10 Torr to about 80 Torr. The flow rate resulting from pumping on the system with mechanical vacuum pump 92 can be in the range of from about 0.5 liters per minute to about 30 liters per minute. NO analysis system 90 can be a light absorption spectrometer, such as a mid-infrared tunable laser absorption spectrometer.

Figure 6:
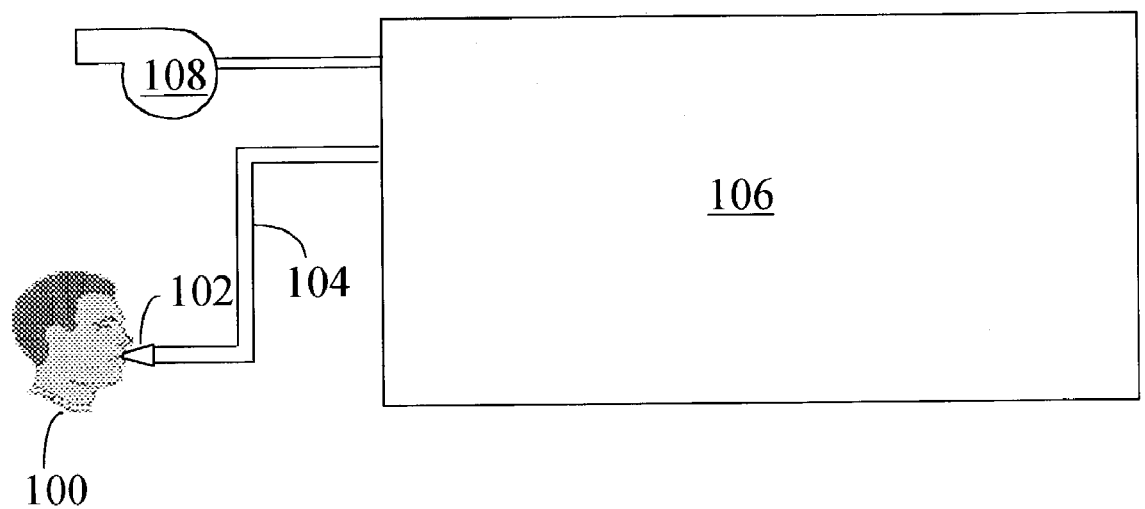
FIG. 6 is a schematic drawing of a breath collection and analysis apparatus.

The invention provides a method and apparatus to measure NO concentration in orally exhaled human breath wherein a single breath is delivered to an NO light absorption spectrometer system through a tube maintained at a reduced pressure provided by a vacuum pump so that the patient need only provide a single breath exhaled normally through the mouth. FIG. 6 shows human subject 100 orally exhaling a single breath as he or she would do when breathing normally into mouthpiece 102 connected to flow tube 104. All orally exhaled breath enters NO light absorption spectrometer analysis system 106 through flow tube 104. Mechanical vacuum pump 108 is connected to NO light absorption spectrometer system 106 and flow tube 104 so that orally exhaled human breath flows through the NO light absorption spectrometer system. Mechanical vacuum pump 108 can be operated to produce a vacuum in the range of from about 20 Torr to about 80 Torr. The flow rate resulting from pumping on the system with mechanical vacuum pump 108 can be in the range of from about 0.5 liters per minute to about 30 liters per minute. NO light absorption spectrometer system 106 can be a mid-infrared tunable laser absorption spectrometer.

The invention provides a method and apparatus to measure NO concentration in orally exhaled human breath wherein a single breath is delivered to an NO analysis system through a tube at a reduced pressure provided by a vacuum pump at two different flow rates, a first flow rate and then at a second flow rate less than the first flow rate so that the patient need only provide a single breath exhaled normally through the mouth. The flow rates can be adjusted using the spectrometer computer. The time that the first flow rate is used can be in the range of from about 0.1 sec to about 10 sec. The second flow rate can be used for a time in the range of from about 5 sec to about 20 sec.

Figure 7:
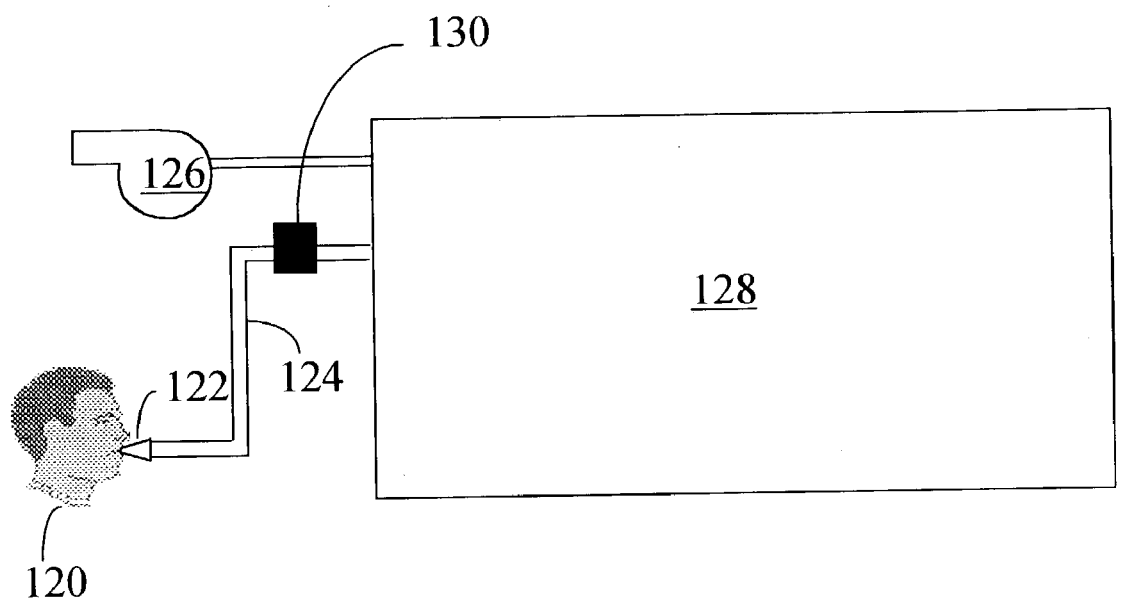
FIG. 7 is a schematic drawing of a breath collection and analysis apparatus including a flow controller.

FIG. 7 shows human subject 120 orally exhaling a single breath as he or she would do when breathing normally into mouthpiece 122 connected to flow tube 124. Mechanical vacuum pump 126 is connected to NO analysis system 128 and flow tube 124 so that orally exhaled human breath flows through NO analysis system 128. Flow controller 130 can be adjusted using a computer in NO analysis system 128 to provide a desired flow rate. The first flow rate is in the range of from about 2 liters per minute to about 30 liters per minute and the second flow rate is in the range of from about 0.5 liters per minute to about 20 liters per minute. NO analysis system 128 can be a light absorption spectrometer, such as a mid-infrared tunable laser absorption spectrometer.

EXAMPLE 1

The following example describes a liquid-$N_2$-free TLAS system equipped with a IV–VI laser operating near 5.2 µm for the purpose of analyzing eNO and exhaled $CO_2$ (e$CO_2$) simultaneously in expired breath. The system required no consumables other than disposable mouthpieces for breath analysis. Absorption measurements were performed using a 107-meter multipass White cell with a 16-liter volume. A closed-cycle cryogenic refrigerator was used to maintain cryogenic laser operating temperatures below 120 K. These refrigerators can dissipate about 5 watts of power at typical laser heat sink temperatures of ~90 K. IV–VI lasers are well suited for cooling with such a system since they typically generate less than 1 watt of waste heat. The system further takes advantage of the ability of a single IV–VI laser to measure $H_2O$, $CO_2$, and NO simultaneously, thereby eliminating any need for introduction of additional calibration gases not originally present in the sample, reference cells, and reference detectors. A breath collection apparatus was fabricated to collect and sample breath in close accordance with the recommendations of the American Thoracic Society. Daily breath measurements from 5 individuals over a period of ten working days were performed. Daily eNO concentrations measured from the 5 individuals calculated using e$CO_2$ end-tidal absorption magnitudes as a reference are compared to concentrations obtained by comparison with a calibrated NO gas standard. The effect of elevated NO levels in the ambient air on calculated eNO concentrations using e$CO_2$ as an internal reference was also studied. To test the flexibility of the internal calibration scheme and to simulate measurements of a child's breath, an adult's breath was measured at different exhalation times from 5 to 20 seconds.

Figure 3:
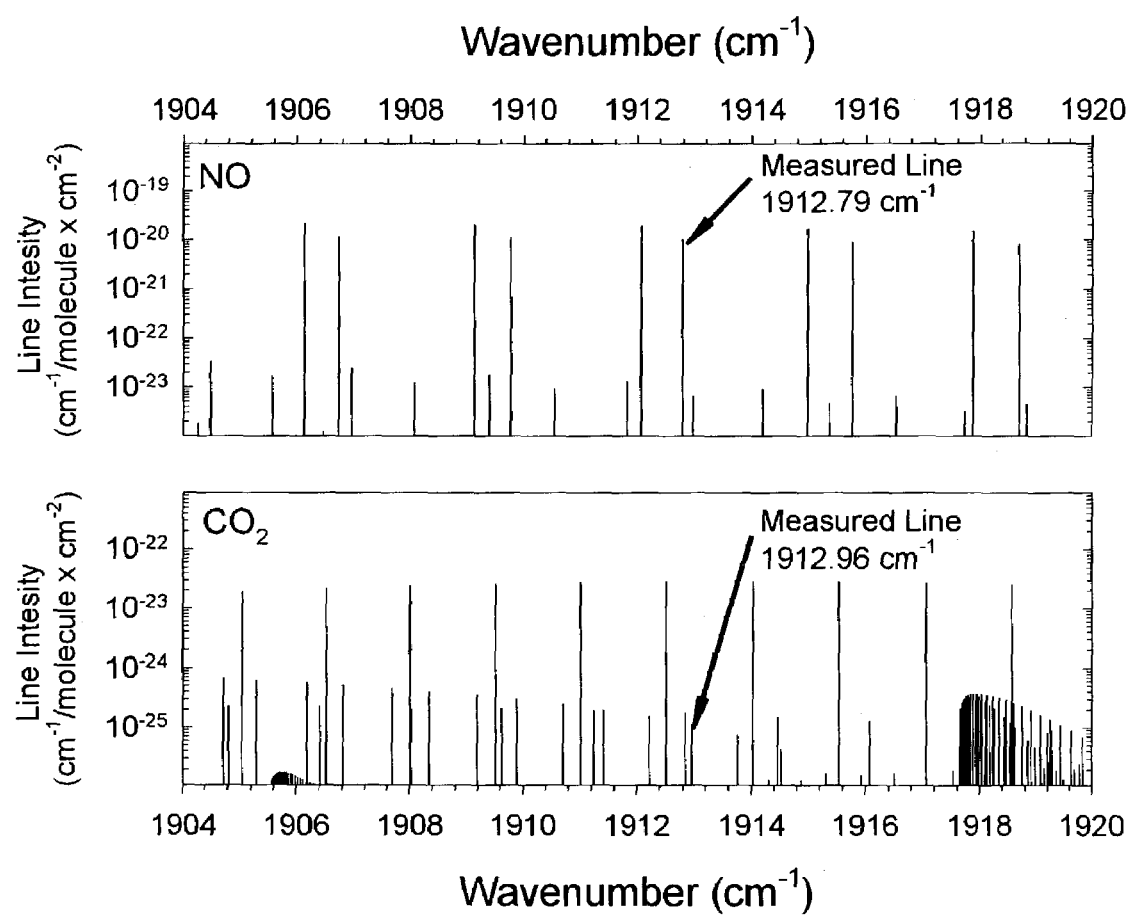
FIG. 3 is a plot of nitric oxide (NO) and carbon dioxide ($CO_2$) absorption line intensities in the 5.2 μm region of the infrared spectrum using data from the HITRAN '96 database.

A brief discussion of specific absorption line attributes for the molecules of interest (NO, $CO_2$, and $H_2O$) between 1912.5 $cm^{-1}$ and 1913.0 $cm^{-1}$ is given. The R(10.5) NO lines located between 1912.7937 $cm^{-1}$ and 1912.7956 $cm^{-1}$ have a maximum absorption intensity of $1.032 \times 10^{31}$ $cm^{-1}/(molecule \cdot cm^{-2})$ and are separated by 0.05 $cm^{-1}$ from the nearest $H_2O$ and $CO_2$ absorption lines. The single $CO_2$ absorption line P(6) at 1912.96 $cm^{-1}$) was measured and has a modest intensity of above $1.134 \times 10^{-25}$ $cm^{-1}/(molecule \cdot cm^{-2})$. There is a second measurable $CO_2$ line located at 1912.69 $cm^{-1}$ with intensity of $1.009 \times 10^{-26}$ $cm^{-1}/(molecule \cdot cm^{-2})$. Also measured simultaneously along with $CO_2$ and NO is $H_2O$ that has a strong absorption line located at 1912.5 $cm^{-1}$ with an intensity of $1.110 \times 10^{-23}$ $cm^{-1}/(molecule \cdot cm^{-2})$. This unambiguous absorption is visible in exhaled breath and in ambient air. The 5.2 µm region contains adequate separation between NO, $CO_2$ and $H_2O$ lines due mainly to the narrow spectral line widths of IV–VI laser emission. The NO and $CO_2$ absorption lines of interest between 1870 $cm^{-1}$ to 1940 $cm^{-1}$ obtained from the HITRAN database are shown in FIG. 3. There exist other possible candidate NO and $CO_2$ absorption lines for simultaneous measurements without interference from each other between 1895 $cm^{-1}$ and 1925 $cm^{-1}$, which are adequate for the eNO breath analysis procedure as described herein.

The TLAS system 41 is shown in FIG. 4. A single IV–VI laser 42 (Ekips Technologies, Norman, Okla.) with typical optical output power of 300 µW was mounted to a temperature-controlled stage not shown inside sealed cryostat 46 kept at cryogenic temperatures using a closed-cycle cryogenic refrigerator, not shown, rated for continuous maintenance free operation (CryoTiger™, APD Cryogenics, Allentown, Pa.) and pumped by ion pump 43. A laser beam represented by line 48 emitted from the IV–VI laser was first directed through a ZnSe window, not shown, and onto off-axis-parabolic mirror (OAPM) 50 to collimate the beam. A combination of flat and concave mirrors 52 was used to direct beam 48 through a 107-meter multipass White cell 54 (Infrared Analysis, Anaheim, Calif.). Upon exiting White cell 54, beam 53 was focused using ZnSe lens 55 and passed through a ZnSe window not shown onto HgCdTe mid-IR photovoltaic detector 56 also located inside cryostat 46. An integrated heater and temperature controller (Lakeshore, Westerville, Ohio), not shown, maintained stable laser operating temperatures at 102 K with an accuracy of ±0.01 K.

A low noise laser current driver in current driver and function generator assembly 58 controlled by personal computer 64 as indicated schematically by arrow 61 supplied currents between 800 mA and 900 mA. A sawtooth voltage ramp of 40 Hz and 0.11 $V_{pp}$ was used to tune the single mode laser emission from 1912.5 $cm^{-1}$ to 1913.0 $cm^{-1}$. Superimposed onto the sawtooth ramp is a smaller triangle waveform at 26.5 kHz and 0.01 $V_{pp}$ to modulate the laser emission frequency. The output of photovoltaic detector 56 is preamplified before a commercial lock-in amplifier 60 (Stanford Research Systems, Sunnyvale, Calif.) sampled the signal at twice the modulation frequency, a scheme known as second harmonic (2f) detection. A TTL signal from the 40 Hz ramp waveform generator was used to trigger the analog-to-digital (A/D) acquisitions of the output signal from the lock-in amplifier. Personal computer 64 controlled a 12-bit A/D converter card (National Instruments, Austin, Tex.) and acquired 500 data points per scan at a sampling frequency of 20 kHz. To reduce high frequency noise, 75 consecutive scans were co-averaged and then sent through a digital low pass Butterworth filter. The largest source of optical noise in the system was etalon fringes originating in White cell 54 and system optics.

Figure 8:
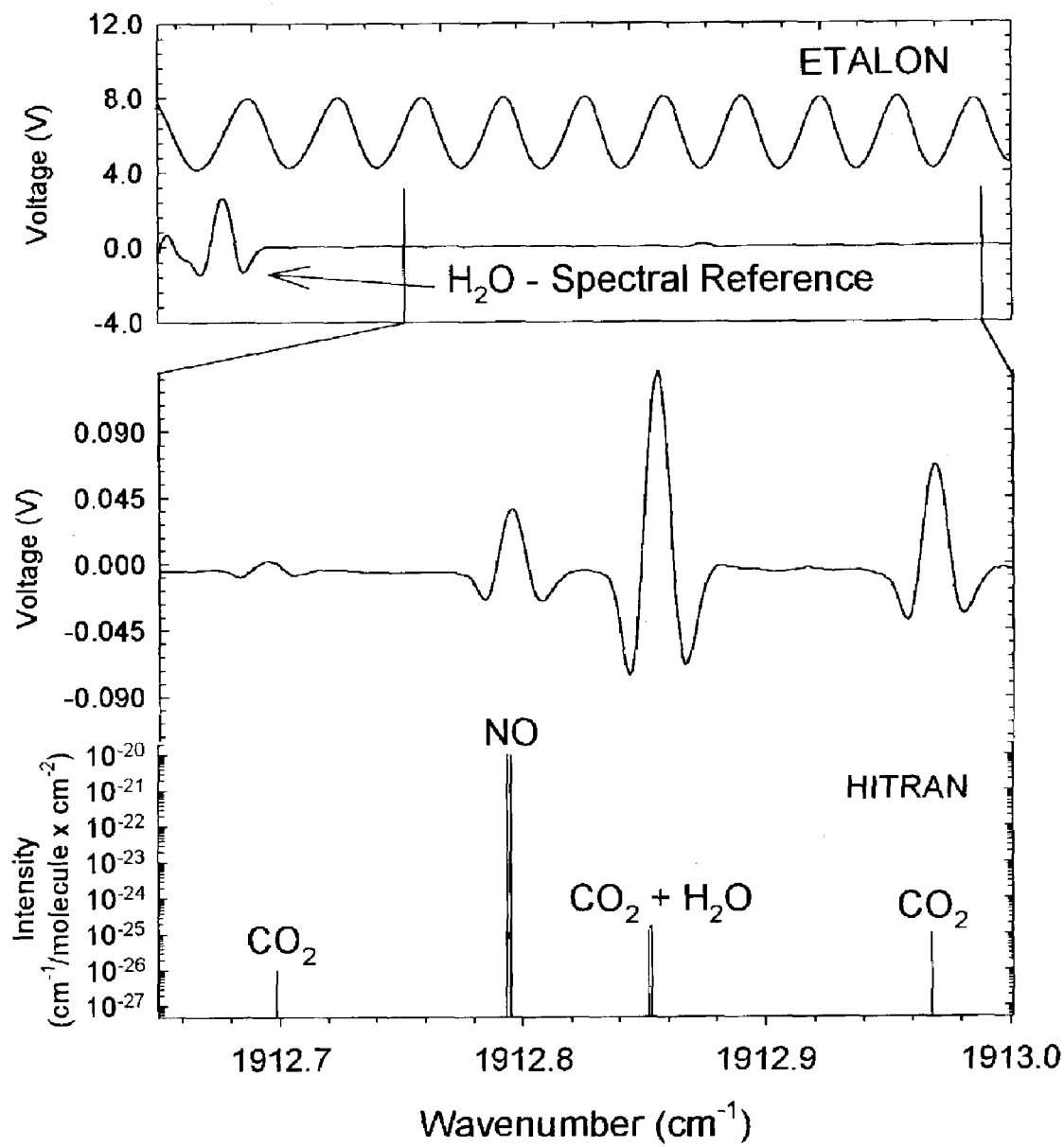
FIG. 8 is a second harmonic spectrum of exhaled alveolar-enriched human breath measured between 1912.5 $cm^{-1}$ and 1913.0 $cm^{-1}$ showing absorption features for NO and $CO_2$.

Spectral shifting of the spectrum can occur due to slight temperature variations of the heat sink for the laser. To counteract this shifting effect, the $H_2O$ absorption peak at 1912.5 $cm^{-1}$ shown in FIG. 8, was used as a spectral reference to line up each spectrum before co-averaging to reduce smear and improve detection sensitivities. A custom software program was used to control the external functionalities of lock-in amplifier 60, function generators and current driver part of assembly 58 using IEEE-488.2 GPTB communications. The software also performed the co-averaging, filtering, and spectral analysis algorithms for determining concentrations based on breath $eNO/eCO_2$ ratios. A second harmonic spectrum of human breath containing peaks for NO, $CO_2$, $H_2O$, and associated HITRAN absorption line strengths is shown in FIG. 8.

Figure 9:
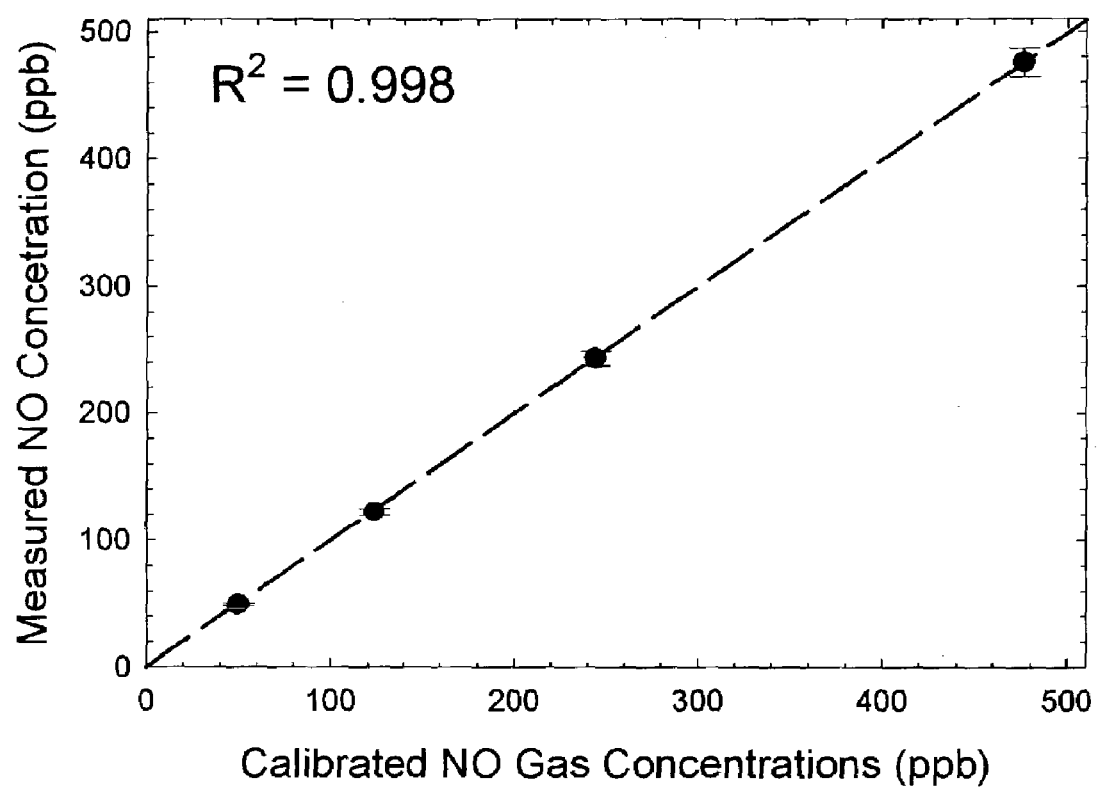
FIG. 9 is gas calibration curve obtained by measuring concentrations of NO produced using a gas dilution system.
Figure 10:
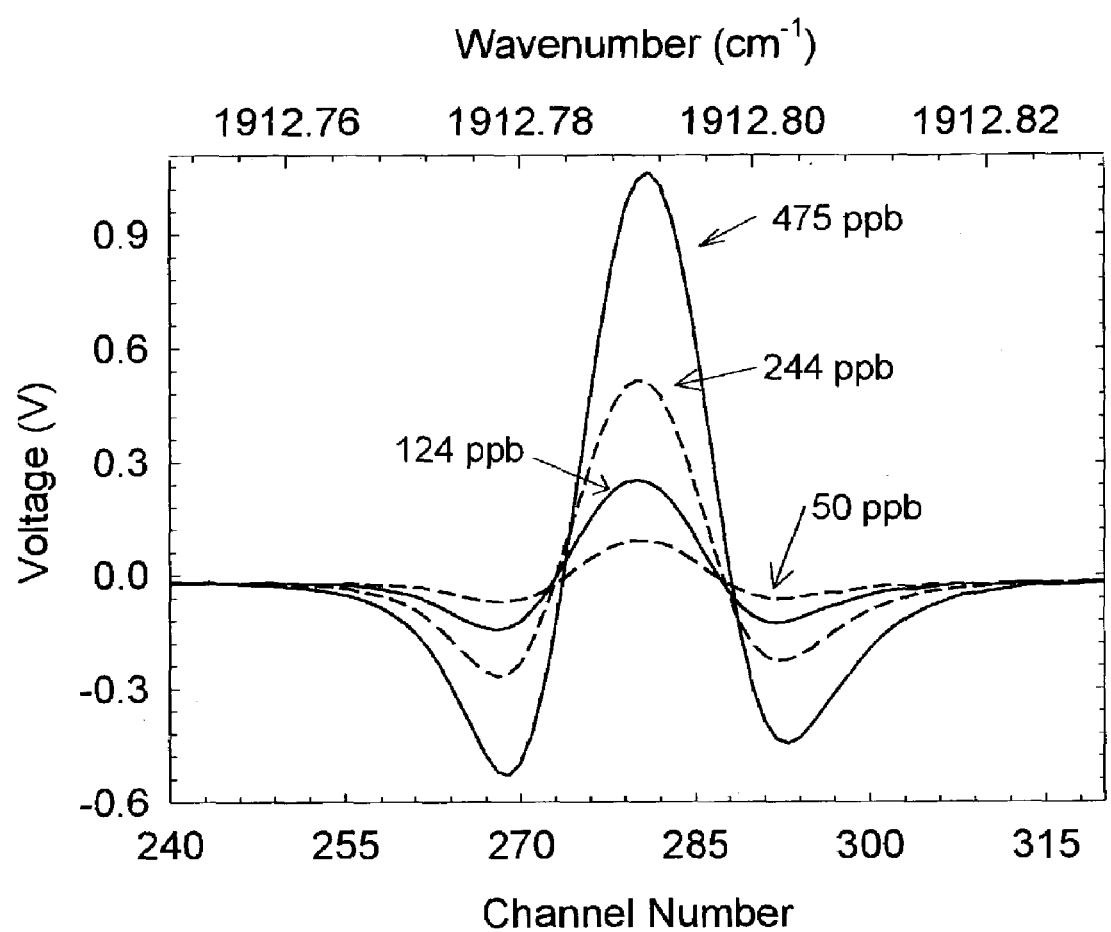
FIG. 10 is a plot showing measured second harmonic absorption of NO (1912.79 $cm^{-1}$) for NO concentrations of 50 ppb, 124 ppb, 244 ppb, and 475 ppb.

Second harmonic spectra contain absorption magnitudes that are directly proportional to concentrations of the associated molecular species. A calibration curve of the instrument was generated using a gas dilution system, which is designed for diluting a 10 ppm±2% NO gas standard (Airgas, Mobile, Ala.), with purified $N_2$. Mass flow controllers located at the inlet to the White cell were used to mix various flows of NO with $N_2$ to achieve continuous flow concentrations from 10 ppm down to 20 ppb. To quantify concentrations, a comparison spectrum was collected at a known concentration of 50 ppb. The absorption magnitude of a 50 ppb NO comparison spectrum was then compared to subsequent absorptions of NO at diluted concentrations down to 20 ppb using a least squares fitting routine which will subsequently be described in detail. The least-squares fitting routine returned the average absorption intensity over the entire absorption characteristic including both negative lobes, which is more accurate than just measuring the peak of the absorption. The calibration curve showing diluted NO gas standard calibrations vs. measured NO is shown in FIG. 9. The error bars for the points in FIG. 9 represent the standard deviation over 200 consecutive data points measured at each calibration concentration. The line shapes at differing concentrations are shown in FIG. 10. Measured NO absorption magnitudes have a strong linear relationship ($R^2$=0.998) with calibrated NO concentrations. The minimum detection limit for a 4 second integration time (75 co-adds) was determined to be 1.5 ppb based upon the $V_{RMS}$ noise in the baseline of the second harmonic spectrum. Further improvement of this figure of merit is possible using faster electronics to collect more spectra in a given time period.

Breath measurements were performed at a pressure of 13 Torr to reduce line broadening and interference between NO, $CO_2$ and $H_2O$. Mechanical vacuum pump 64 including pump exhaust 65 shown in FIG. 10 induced flow through the gas cell at a constant rate of 2 L/minute using flow controllers, not shown. This rate of gas suction was comfortable for patients exhaling into the system over a period of 20 seconds or less. The breath collection device (Quintron, Milwaukee, Wis.) was designed to collect single-exhalations and consisted of T piece 66 connected to disposable mouthpiece 68, 500 mL discard bag 70, and ¼" diameter Teflon tubing 72 directing breath through flow controllers not shown and into White cell 54. The discard bag accepted the first 500 mL of breath at little to no breathing resistance. This headspace breath contains a high concentration of NO originating from the nasal cavity. The remaining exhaled air enters the Teflon tubing at a constant rate of 2 L/min. Volunteers were instructed to exhale a single breath with force, which assisted in closing the velopharyngeal aperture limiting the entry of nasal NO via the posterior nasopharynx. A one-way flutter valve not shown located at the entrance to the discard bag prevented headspace breath from re-entering the breath collection system, and the discard bag was manually emptied after each exhalation. All breath measurements given in this report are single breath exhalations for 20 seconds unless otherwise stated. Institutional Review Board approval was granted from the University of Oklahoma for human subjects research and each participant signed an informed consent form prior to donating breath.

Figure 11:
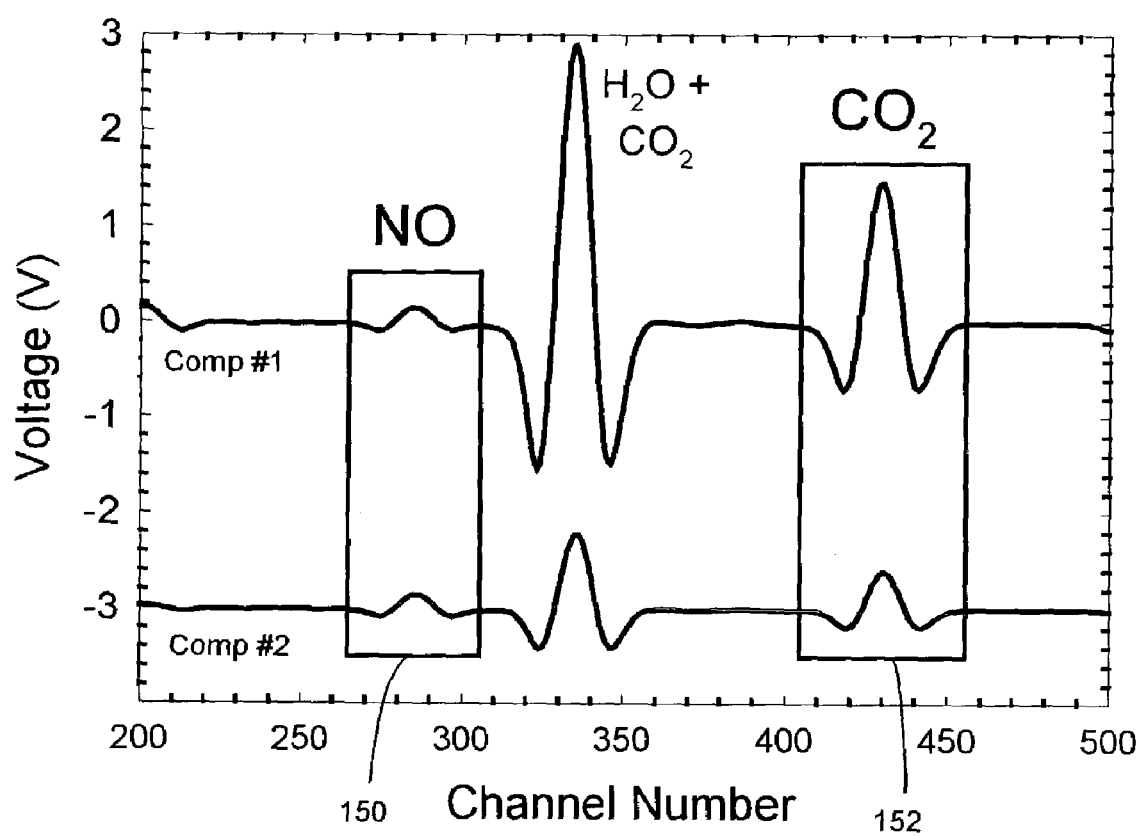
FIG. 11 is a plot showing two comparison spectra (Comp. #1 and Comp. #2) at varying unknown concentrations of NO and $CO_2$.

The magnitude of absorption due to breath eNO and $eCO_2$ was determined using a least-squares fitting routine, which uses a comparison spectrum to analyze measured spectra during breath testing. Two comparison spectra, denoted as #1 and #2, at unknown different concentrations of NO and $CO_2$ are shown in FIG. 11. The rectangular windows encompassing the NO and $CO_2$ absorption define the windows 150 and 152, respectively, used to compare the comparison spectra to the measured spectra and encompass both negative lobes and the absorption peak. To characterize the relationship between the NO and $CO_2$ absorption profiles within each comparison, background spectra were subtracted from each comparison spectrum to eliminate any baseline offset. Next, the peak absorption voltages were determined to obtain a voltage ratio, $(V_{NO}/V_{CO_2})$.

During breath donations, measured spectra containing the absorption for eNO and $eCO_2$ were compared to either comparison spectrum #1 or #2 using the least squares fitting routine. The measured absorption line contained in the set window for the sample (Y) and the comparison (X) have a linear relationship of the form $Y_j=a+bX_j$. Here, X and Y are the measured voltage amplitudes within a window containing the entire absorption characteristic including the negative lobes and some baseline on either side. The amplitude scaling factor, b, represents the absorption magnitude determined using the least squares method shown in Equation (1). The coefficient, a, represents baseline offset and is ignored. The index, j, in Equation (1) represents the position of the channel number in acquired spectra as shown in FIG. 10.

$$b = \frac{(\sum Y_j)(\sum X_j) - N(\sum X_j Y_j)}{(\sum X_j)^2 - N(\sum X_j^2)} \quad (1)$$

Figure 12:
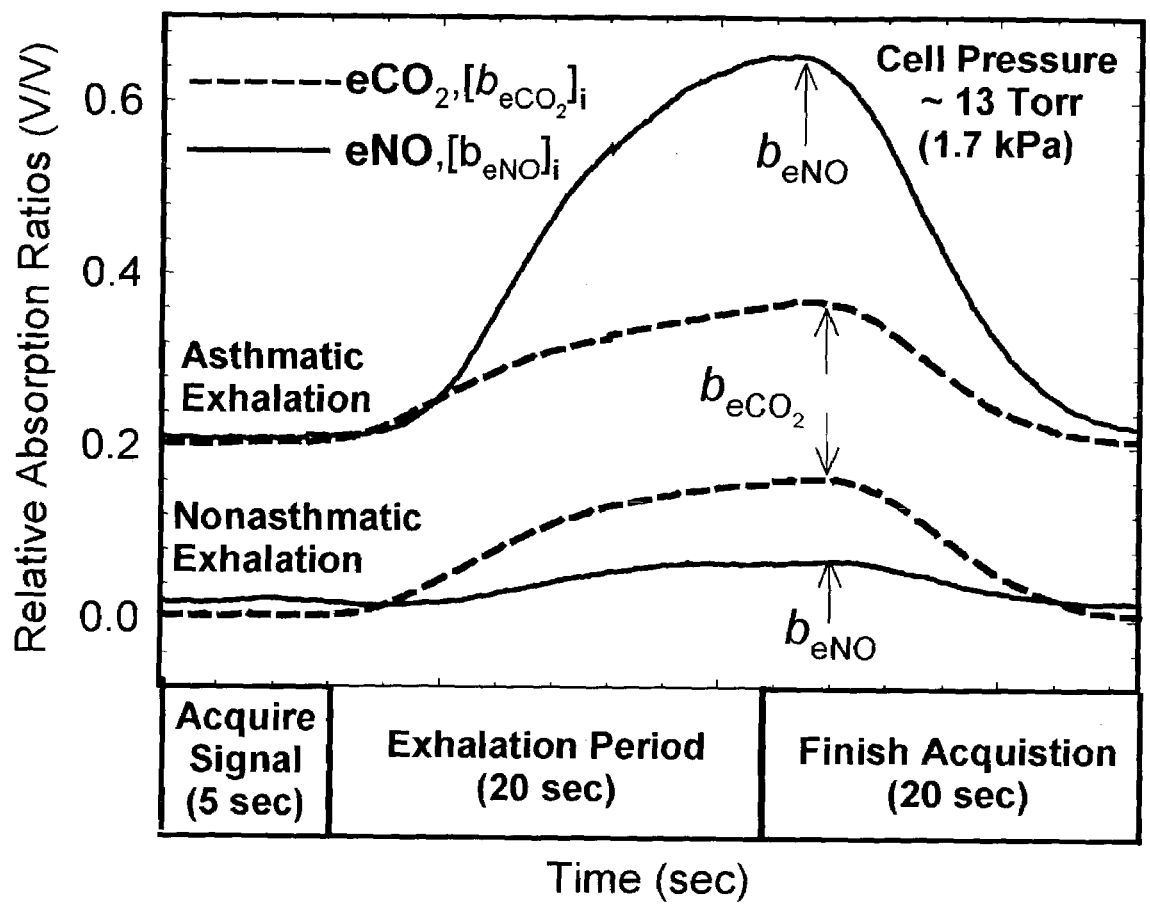
FIG. 12 is a plot showing exhalation trends over a 20 second exhalation of eNO and $eCO_2$ measured from an asthmatic subject and a nonasthmatic subject.

Example eNO and $eCO_2$ absorption magnitude arrays over time obtained for 20-second breath donations from a nonasthmatic and asthmatic volunteer are shown in FIG. 12. The end-tidal (or maximum) values in the plot of FIG. 12 occur after the end of the exhalation period because of short delays from gas exchange and software processing overhead. Prior to exhalation, 5 seconds of NO and $CO_2$ measurements are performed and averaged to determine their absorption magnitudes in the ambient air. The absorption magnitude for $eCO_2$, $b_{eCO_2}$, is determined by taking the end-tidal value in the exhalation trend array, $[b_{eCO_2}]_i$. The index, i, in the exhalation trend array denotes absorption magnitude data points collected over the breath analysis period. The maximum $b_{eCO_2}$ value is used to verify correct breath donation. This works as a good verification because $eCO_2$ concentrations are always greater than $CO_2$ concentrations in the ambient air. The absorption value in the $[b_{eNO}]_i$ array measured during the exhalation period that most deviates from the established baseline absorption magnitude for NO in the ambient is used to determine $b_{eNO}$. For determining $b_{eNO}$, it is not proper to use only the maximum value in $[b_{eNO}]_i$ because it is possible to have larger NO concentrations in the ambient air than in exhaled breath. Once $b_{eNO}$ and $b_{eCO_2}$ have been determined, equation (2) is used to describe the overall absorption ratio, $A_{eNO}/A_{eCO_2}$, relating the measured absorption magnitudes of analyzed breath samples to the voltage magnitudes of the comparison spectra.

$$\frac{A_{eNO}}{A_{eCO_2}} = \frac{b_{eNO}}{b_{eCO_2}} \times \frac{V_{NO}}{V_{CO_2}} \quad (2)$$

Utilizing known standard absorption line strengths (S(v)) and pressure broadening coefficients (g) found in the HITRAN database, equation (3) can be used to relate the concentrations of eNO and $eCO_2$ in breath, where $C_{eNO}$ and $C_{eCO_2}$ represent the concentration of eNO and $eCO_2$, respectively.

$$C_{eNO} = \left(\frac{A_{eNO}}{A_{eCO_2}}\right)\left(\frac{g_{NO}}{g_{CO_2}}\right)\left(\frac{S(v)_{CO_2}}{S(v)_{NO}}\right) \times C_{eCO_2} \quad (3)$$

Equation (3) was derived using Beer's law and the fact that second harmonic spectra produce absorption magnitudes that have an approximate linear relationship with the concentration of the absorbing gas species. Equation (3) assumes that laser power is equivalent across both the NO and $CO_2$ absorption lines. To solve for $C_{eNO}$, it is assumed that $eCO_2$ concentrations are 4% since the typical value for exhaled $C_{eCO_2}$ in human breath is in the range of from about 4% to about 5%. Equation (3) is vulnerable to error if actual $C_{eCO_2}$ from an individual significantly deviates from the foregoing range. Slight variations (±10%) in actual $C_{eCO_2}$, however, do not significantly affect the interpreted results because there is not a critical clinical importance at this time in obtaining high precision eNO concentrations. A 10% variation in $eCO_2$ concentration would give a typical error of about ±2 ppb in the calculated eNO concentration, which is much smaller than the difference between the eNO concentration ranges for asthmatics (30 ppb to 80 ppb) and non-asthmatics (5 to 20 ppb).

Results of testing five individuals (four nonasthmatics and one asthmatic) using comparison spectra #1 and #2 over a period of 10-days are presented. Calibrated eNO levels are compared to calculated eNO concentrations using equation (3). Also given are the results of studying different breath testing parameters including differing exhalation times, White cell pressures, and ambient NO levels.

Figure 13:
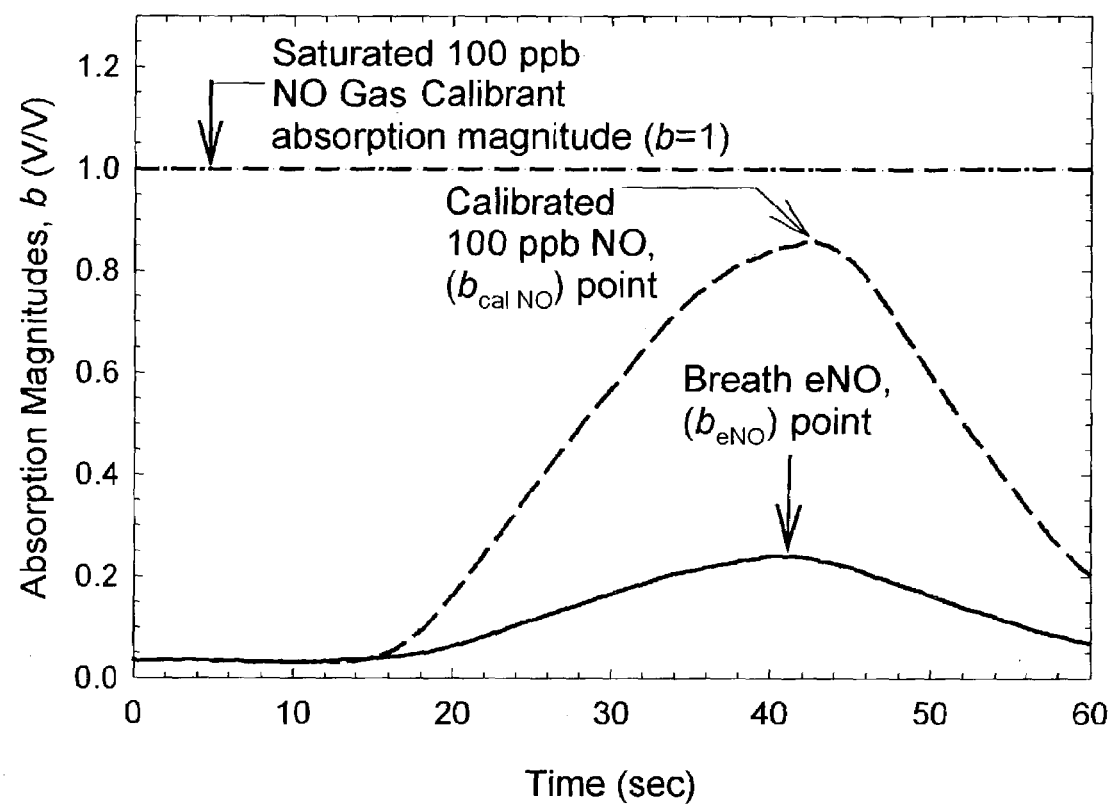
FIG. 13 is a plot showing absorption magnitude of NO vs. time for 100 ppb NO gas flowed through a spectrometer gas sample cell for 20 seconds and for a subject's breath for a 20 second exhalation.

For comparison spectrum #1, each participant gave three breaths and the calculated eNO results using equation (3) were averaged over the three breaths. The same procedure was repeated using comparison spectrum #2. To perform calibration measurements for each participant, a diluted NO standard of 100 ppb was flowed through White cell 54 for 20 seconds, just as if a participant was exhaling. FIG. 13 shows a representative example concentration trend for calibrated NO flowing through the gas cell. The 100 ppb NO signal over the 20 second period was compared to a reference spectrum collected while White cell 54 was saturated with 100 ppb NO and the associated average absorption magnitude (b) was ~1.0, as indicated in FIG. 13. The 100 ppb NO sample flow for 20 seconds does not completely saturate the White cell volume of 16 L at a gas exchange rate of 2 L/min, and a small software time constant due to data computational overhead does not allow $b_{cal\ eNO}$ to completely reach 1.0. Immediately following analysis of the 100 ppb NO calibration gas, the volunteer exhaled into the system and the absorption magnitude for $b_{eNO}$ was then compared to the 20 second 100 ppb calibration NO absorption magnitude, $b_{cal\ NO}$. The calibrated eNO concentration, $C_{cal\ eNO}$, was calculated using equation (4).

$$C_{caleNO} = \left(\frac{b_{eNO}}{b_{calNO}}\right) \times (100 \text{ ppb Reference NO}) \quad (4)$$

Three sequential calibrated eNO breath measurements were performed and averaged to determine the calibrated eNO concentration, $C_{cal\ eNO}$. It should be noted that a 16 L cell volume is suitable when discarding headspace, but smaller cell volumes are more desirable for rapid gas exchange rates and improved temporal resolution.

Figure 14:
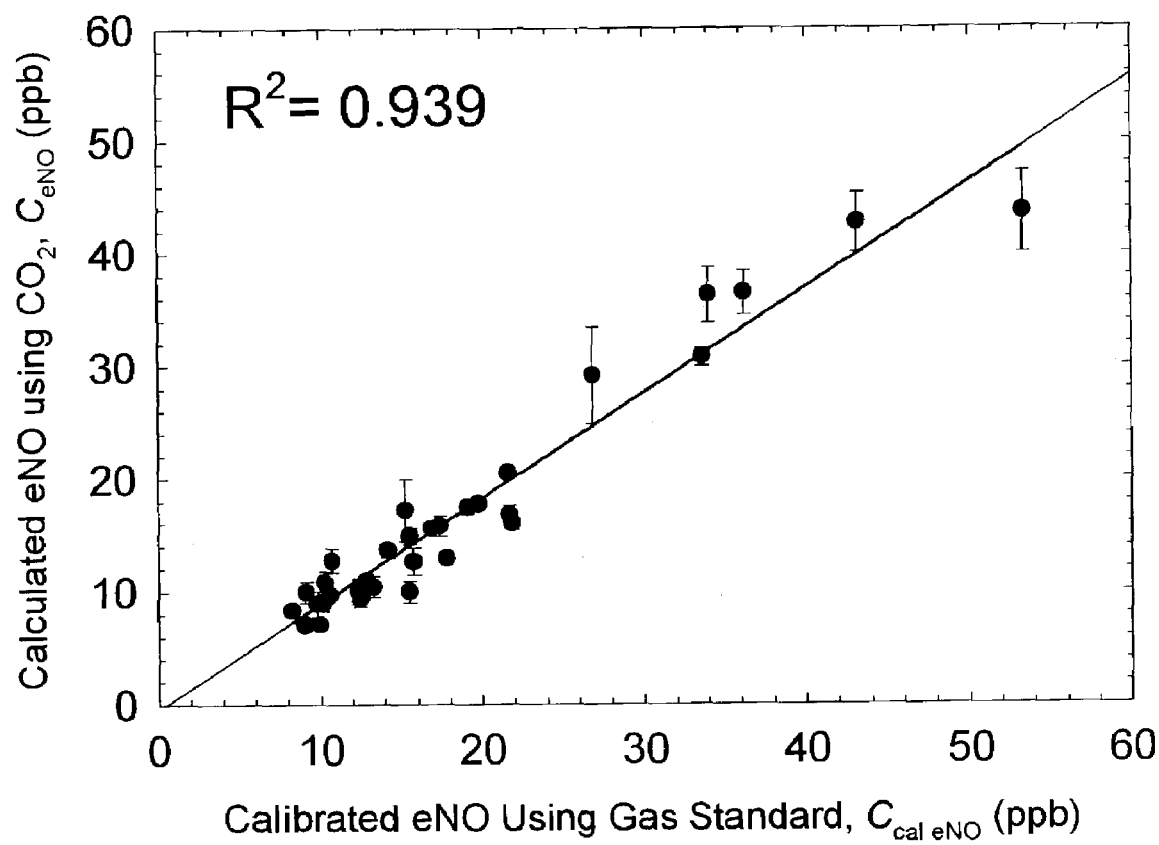
FIG. 14 is a plot of calibrated eNO breath measurements quantified using a 50 ppb NO gas standard versus eNO concentrations calculated using the $eCO_2$ absorption magnitudes and Equation (3).

The five participants donated nine breaths daily over the period of ten working days (three breaths for comparison spectrum #1, three breaths for comparison spectrum #2, and three breaths for calibration). The relationship between calibrated eNO results vs. the calculated eNO results for comparison spectra #1 and #2 over the ten-day period are shown in FIG. 14 with error bars. There was a good linear relationship ($R^2=0.939$) between the two methods showing that equation (3) using a 4% value for $eCO_2$ concentrations allowed accurate eNO measurements over the two-week testing period.

Figure 15:
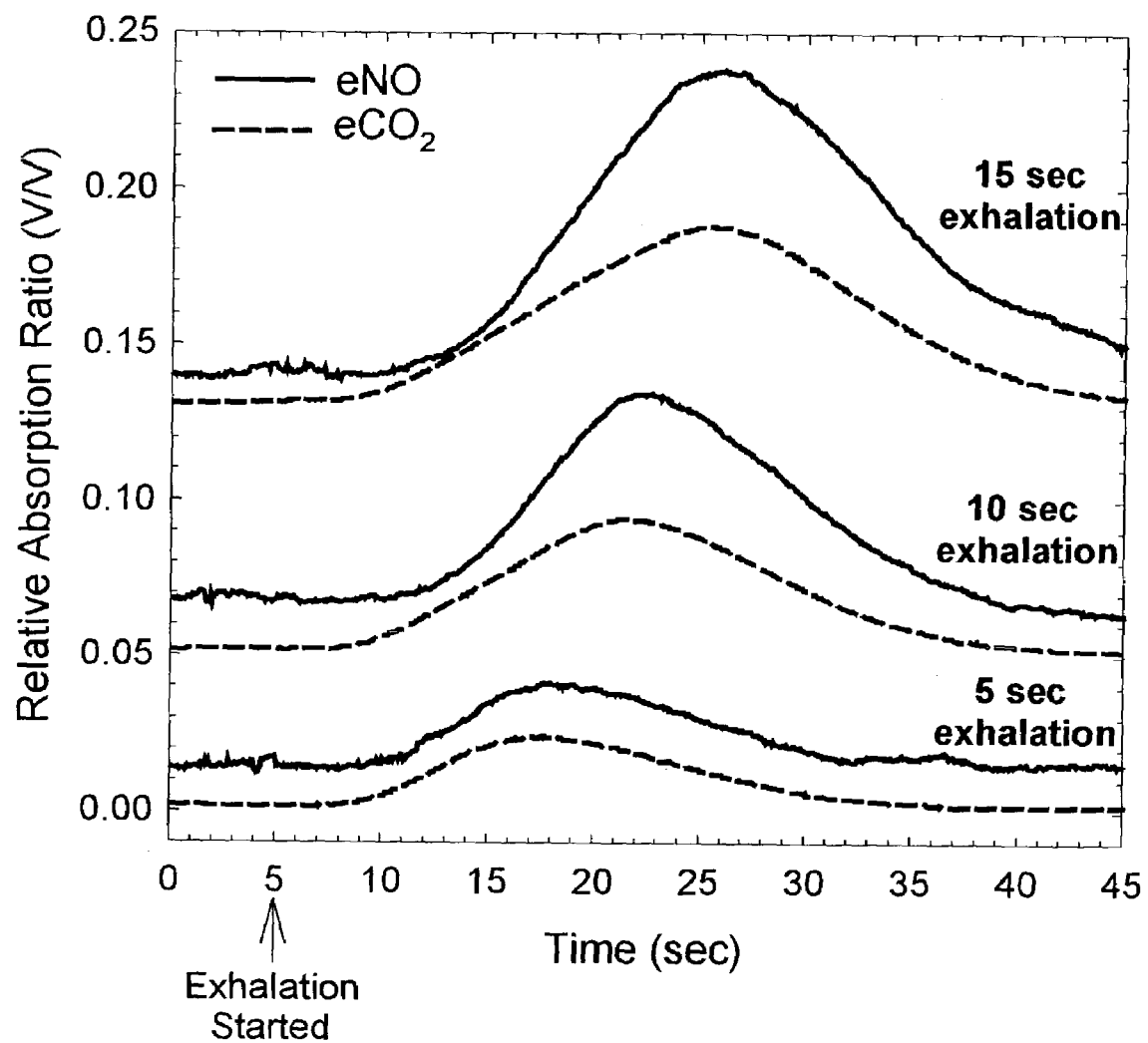
FIG. 15 is a plot showing absorption magnitudes of eNO and $eCO_2$ as a function of time for varying exhalation times of 5, 10 and 15 seconds.

Adults found the 20 second exhalation time comfortable using a constant 2 L/min flow rate. The young, elderly, or ill, however, may find a 20 second exhalation period too long. FIG. 15 shows the results of an adult participant exhaling for periods of 15, 10 and 5 seconds, which would simulate breath collection from a child or adult with limited lung function. The longer the exhalation times, the stronger the measured signals due to more NO and $CO_2$ molecules occupying White cell 54. However, the eNO and $eCO_2$ ratios together help to compensate for variations in exhalation times and resulted in little variation in calculated eNO concentrations using equation (3), as shown in Table I.

Figure 16:
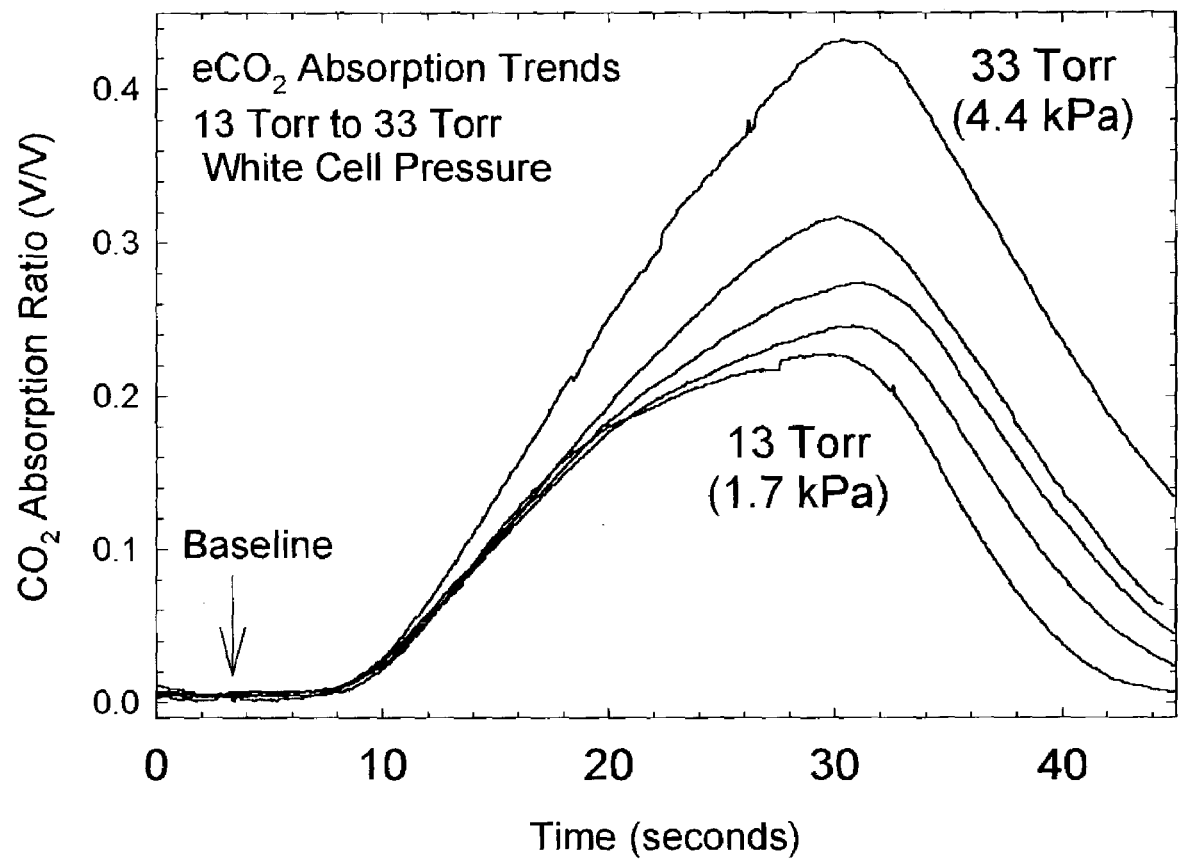
FIG. 16 is a plot of exhalation trends for $eCO_2$ at varying gas sample cell pressures between 13 Torr (1.7 kPa) and 33 Torr (4.4 kPa).
Figure 17:
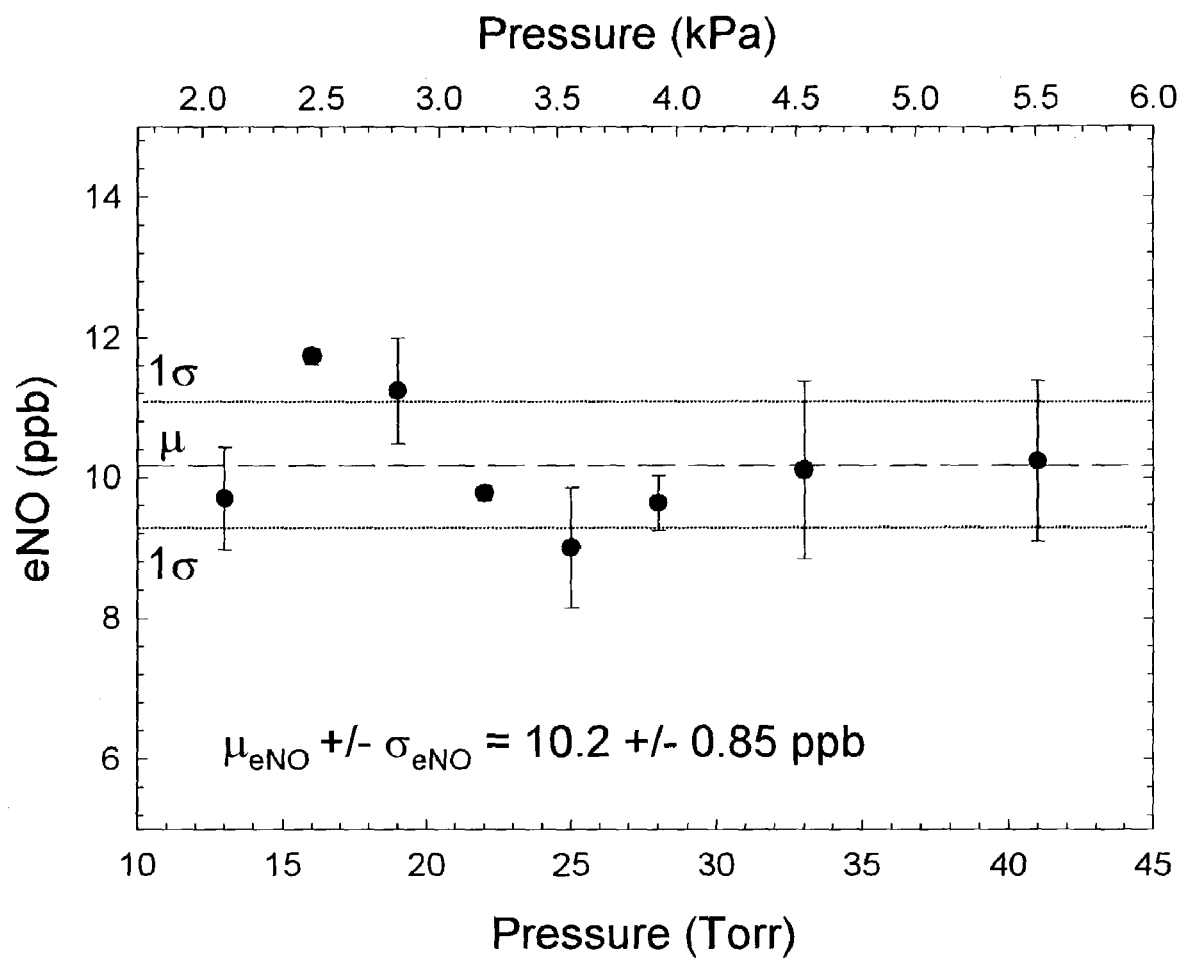
FIG. 17 is a plot of calculated eNO concentrations obtained using Equation (3) at varying pressures between 13 Torr and 40 Torr along with the eNO concentration mean, $\mu_{eNO}$, and standard deviation, $\sigma_{eNO}$.

FIG. 16 shows $eCO_2$ trends from an individual exhaling at sample cell pressures ranging from 13 Torr to 33 Torr. As the pressure increases, the volume increases and the trends have a less apparent plateau because breath is not filling as much of the White cell volume. FIG. 17 shows the calculated eNO results versus pressure. Varying exhalation times and cell pressures do not appear to affect calculated eNO results significantly.

During the early morning and evening rush hours, NO levels in the ambient air have been observed to be as high as 200 ppb, due mainly to automobile exhaust. To test the effect of elevated ambient NO levels on measured eNO values, a volunteer donated breath in the morning when ambient NO levels were high, above 20 ppb, and again in the mid-afternoon when ambient levels were below 5 ppb. FIGS. 18(a) and 18(b) show the eNO and $eCO_2$ trends for both breath donations from the same volunteer. When NO concentrations in ambient air are larger than eNO in breath, breath eNO displaces ambient NO in the cell and the total concentration of NO in the cell goes down. Lower eNO concentrations than ambient NO concentrations suggest inhaled NO from the ambient air is rapidly absorbed by airway tissues and not subsequently exhaled. Recent in vivo measurements of NO and its chemical reaction products in human airways show that NO rapidly consumes reactive oxidative species (ROS) producing less reactive intermediate compounds such as ONOO— and ONOOH. This process leads to the accumulation of the innocuous product $NO_3$—. It is suggested that high eNO levels in the breath of asthma sufferers may actually be associated with a protective mechanism in which production of endogenous NO reduces the concentration of more damaging ROS that are also produced in the airways of individuals with asthma. The observation of exhaled NO concentrations that are lower than ambient levels shows that ambient (exogenous) NO is also rapidly consumed by airway tissues. It is not clear whether or not such consumption in the lungs of healthy or asthmatic individuals is beneficial.

Elevated ambient NO acts as a source of interference when using chemiluminescence; however, the breath collection method of the invention combined with a mid-IR TLAS system provided for repeatable eNO measurements regardless of high or low ambient NO concentrations. Since ambient NO concentrations are not a factor influencing reproducibility, the instrument may be operated in environments where air pollution effects are significant.

EXAMPLE 2

The following example describes how the breath analysis method and apparatus of the invention may be used in a clinical setting to diagnose and monitor the efficacy of treatment of an asthmatic patient with anti-inflammatory therapy.

Figure 19:
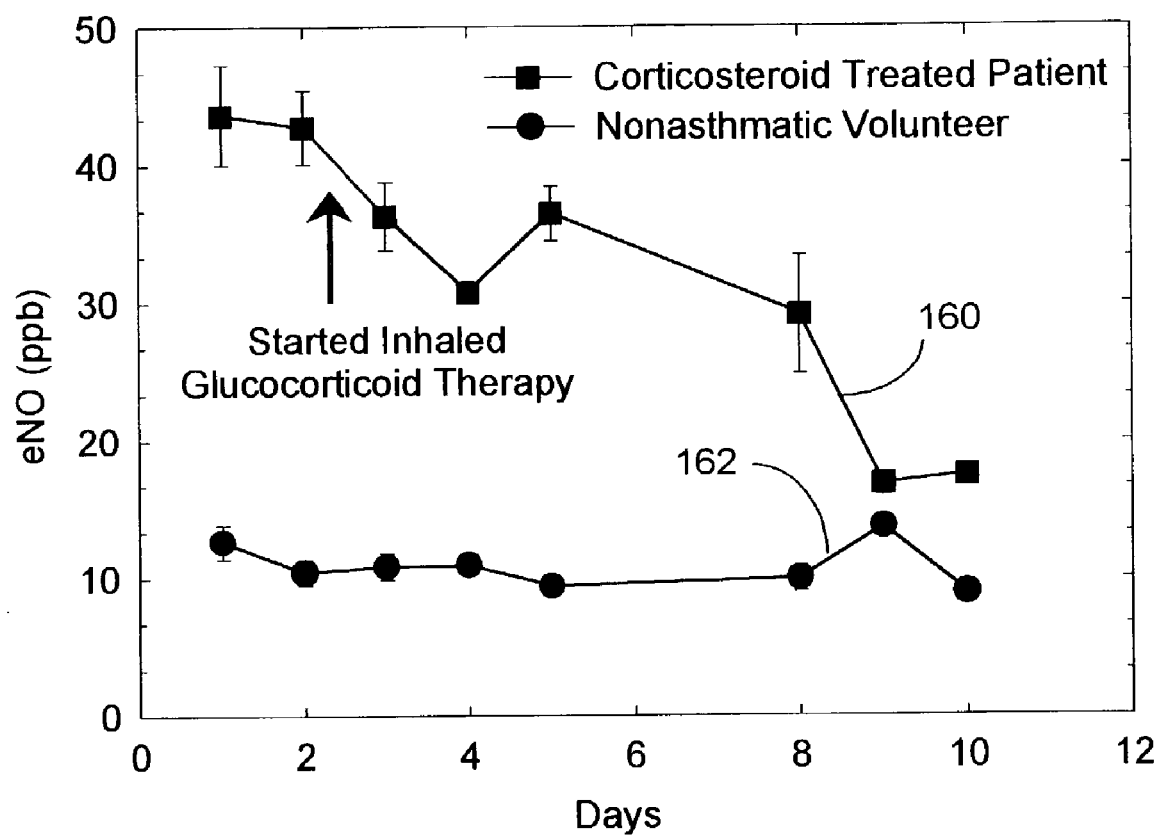
FIG. 19 is a plot showing concentrations of eNO obtained using Equation (3) over a period of 10 days for an asthmatic patient undergoing a corticosteroid treatment regimen and for a non-asthmatic subject over the same time period.

In FIG. 19, lower plot 162 shows eNO concentrations for a healthy volunteer indicating that eNO is below 20 ppb as expected in the absence of disease. Upper plot 160 shows eNO concentrations for a 42-year-old white male who initially did not carry a diagnosis of asthma. He did have a history of severe seasonal allergies including allergic rhinitis. The patient did experience intermittent chest "heaviness", though he denied more obvious symptoms of the disease. His initial spirometry was normal, however, subsequent methacholine challenge testing was positive, indicating hyperactive airways and a likely diagnosis of asthma. The patient's eNO was found to be elevated (>40 ppb) and subsequently a trial of inhaled glucocorticoids was undertaken. As illustrated in FIG. 19, by the nine-day mark, the patient's eNO had dramatically fallen and was in the normal range of below 20 ppb. Despite his initial lack of symptoms, the patient subjectively felt much better when treated with the inhaled glucocorticoids.

Methacholine is a medication that will induce airway obstruction only in the presence of "hyper-reactive" airways. A positive test is indicated by a 20% fall in the measured baseline FEV1 (forced expired volume in one second). This has been the "gold standard" for establishing the diagnosis of asthma, a disease that can be quite variable in its presentation. Despite its utility, the methacholine challenge test is time consuming (~1 hour), cumbersome, expensive to perform, and potentially risky because a bronchoconstrictive drug is administered. It certainly is not suitable for routine monitoring of the asthmatic. Unlike the methacholine test, the eNO test is fast, easy to perform, economical, and presents essentially no risk to the patient. It provides an assessment of underlying airway inflammation, which is a chronic condition in asthma patients. Other asthma diagnostic tests such as spirometry and peak flow measurement evaluate the airway constrictive component of the disease, a typically acute condition which may not be present during a clinical evaluation. The breath analysis method and apparatus of the invention and its ability to determine real-time eNO concentrations with ppb sensitivities provides a reliable clinical tool for the diagnosis and monitoring of asthma.

What is claimed is:

1. A method for assessing human airway inflammation comprising steps of;
   collecting an orally exhaled human breath sample over an exhalation interval, wherein said orally exhaled human breath sample comprises orally exhaled NO and orally exhaled $CO_2$;
   providing a spectrometer including a spectrometer light source, a spectrometer gas sample cell, a spectrometer detector and a spectrometer computer;
   placing said orally exhaled human breath sample in said spectrometer gas sample cell;
   illuminating said orally exhaled human breath sample with a spectrometer light source;
   detecting a transmitted light beam which has passed through said orally exhaled human breath sample with said spectrometer detector to produce a signal sampling;
   generating a human breath sample spectrum from said signal sampling;
   analyzing said human breath sample spectrum using said spectrometer computer, said step of analyzing including identifying an absorption characteristic of orally exhaled NO and an absorption characteristic of orally exhaled $CO_2$, determining an orally exhaled NO absorption intensity and an orally exhaled $CO_2$ absorption intensity, storing said orally exhaled NO absorption intensity and said orally exhaled $CO_2$ absorption intensity as a function of time over the exhalation interval;
   repeating said analyzing and generating to produce a series of gas mixture spectra, each spectrum having an absorption characteristic of the orally exhaled NO and the orally exhaled $CO_2$;
   identifying a single signal sampling interval wherein a known concentration $CO_2$ gas absorption which corresponds to an independently known $CO_2$ gas concentration and a simultaneous NO absorption occur;
   calculating a ratio of said simultaneous NO absorption intensity to said known concentration $CO_2$ gas absorption intensity and multiplying said ratio by a proportionality constant to obtain concentration of said orally exhaled NO thereby providing an assessment of human airway inflammation.

2. The method of claim 1 wherein said collecting step further includes keeping said spectrometer gas sample cell at a pressure selected to reduce line broadening and interference between said exhaled NO absorption and said $CO_2$ absorption in said orally exhaled human breath sample.

3. The method of claim 1 wherein said step of collecting further includes having a human subject exhale a single breath as said human subject would normally exhale including initial exhaled breath and remaining exhaled breath into said spectrometer gas collection chamber wherein said spectrometer gas collection chamber further includes a spectrometer gas cell for said remaining exhaled breath and a discard container to accept said initial exhaled breath thereby preventing said initial exhaled breath from entering said spectrometer gas sample cell.

4. The method of claim 1 wherein said spectrometer is a mid-infrared tunable laser absorption spectroscopy system.

5. The method of claim 4 wherein said laser is a IV–VI diode laser further characterized by an emission wavelength in the range of from about 3 µm to about 10 µm.

6. The method of claim 1 further including placing said exhaled human breath mixture sample in a Herriott cell.

7. The method of claim 1 further including placing said exhaled human breath sample in a multi-pass White cell.

8. The method of claim 1 wherein said step of placing said exhaled human breath in said spectrometer further includes introducing said exhaled human breath sample into said spectrometer gas sample cell and pumping to induce a flow through said spectrometer gas sample cell.

9. The method of claim 1 wherein said human breath sample spectrum is a second harmonic absorption spectrum.

10. The method of claim 1 further comprising performing a running co-average of said NO absorption intensity and a running co-average of the $CO_2$ gas absorption intensity.

11. The method of claim 1 wherein said exhaled human breath is allowed to flow through said spectrometer gas sample cell at a first flow rate and at a second flow rate.

12. The method of claim 11 wherein said first flow rate is greater than said second flow rate and said first flow rate is used before said second flow rate.

13. The method of claim 1 further including identifying a $CO_2$ absorption intensity maximum value and a simultaneous NO absorption intensity value obtained simultaneously during a single signal sampling interval and using said $CO_2$ absorption intensity maximum value and said simultaneous NO absorption intensity value in said calculating a ratio step.

14. The method of claim 13 wherein said $CO_2$ absorption intensity maximum value is associated with an independently known $CO_2$ concentration and said independently known $CO_2$ concentration is in the range of from about 4% to about 5%.

15. The method of claim 1 wherein said concentration of exhaled NO is in the range of from about 5 parts per billion to about 100 parts per billion and indicates airway inflammation.

16. An apparatus for assessing human airway inflammation comprising; a spectrometer gas sample cell adapted to receive an orally exhaled human breath sample containing exhaled NO and exhaled $CO_2$, a spectrometer light source for illuminating said orally exhaled human breath sample, a spectrometer detector for detecting light transmitted through said orally exhaled human breath sample to generate a signal sampling characteristic of the orally exhaled human breath sample, and a spectrometer computer wherein said spectrometer computer further includes an executable program for analyzing a human breath sample spectra generated from the signal sampling by identifying an exhaled NO absorption and an exhaled $CO_2$ absorption, determining an exhaled NO absorption intensity and an exhaled $CO_2$ absorption intensity, storing said exhaled NO absorption intensity and said exhaled $CO_2$ absorption intensity as a function of time, generating a series of human breath sample spectra, each spectrum having an absorption characteristic of the exhaled NO and the exhaled $CO_2$, and to identify a single signal sampling interval wherein a known concentration $CO_2$ gas absorption which corresponds to an independently known $CO_2$ gas concentration variable within an acceptable range and a simultaneous NO absorption occur; calculating a ratio of said simultaneous NO absorption intensity to said known concentration $CO_2$ gas absorption intensity and multiplying said ratio by a proportionality constant to obtain concentration of said exhaled NO thereby providing an assessment of human airway inflammation.

17. The apparatus of claim 16 further including a mouthpiece for accepting said exhaled human breath sample, a T-piece connected to said mouthpiece, and wherein said T-piece is further connected to a discard container to accept initial exhaled human breath and to a tube for transporting remaining exhaled human breath into said spectrometer gas sample cell.

18. The apparatus of claim 17 further including a one-way flutter valve separating said T-piece from said discard container to keep initial exhaled human breath in said discard container.

19. The apparatus of claim 17 further including a vacuum pump connected to said spectrometer gas sample cell for inducing flow of said remaining exhaled human breath through said tube and spectrometer gas sample cell.

20. The apparatus of claim 16 wherein said spectrometer is a mid-infrared tunable laser absorption spectroscopy system.

21. The apparatus of claim 20 wherein said laser is a IV–VI diode laser further characterized by an emission wavelength in the range of from about 3 µm to about 10 µm.

22. The apparatus of claim 16 wherein said spectrometer gas sample cell is a Herriott cell.

23. The apparatus of claim 16 wherein said spectrometer gas sample cell is a multi-pass White cell.

24. The apparatus of claim 16 wherein said executable program further includes instructions for identifying a $CO_2$ absorption intensity maximum value and a simultaneous NO absorption intensity value obtained simultaneously during a single signal sampling interval and using said $CO_2$ absorption intensity maximum value and said simultaneous NO absorption intensity value to calculate said ratio.

25. The apparatus of claim 24 wherein said $CO_2$ absorption intensity maximum value is associated with an independently known $CO_2$ concentration and said independently known $CO_2$ concentration is in the range of from about 4% to about 5%.

* * * * *